US006824890B2

(12) United States Patent
Bazan et al.

(10) Patent No.: US 6,824,890 B2
(45) Date of Patent: Nov. 30, 2004

(54) SOLUBLE TETRAHEDRAL COMPOUNDS FOR USE IN ELECTROLUMINESCENT DEVICES

(75) Inventors: Guillermo C. Bazan, Santa Barbara, CA (US); Shujun Wang, Bedford Hills, NY (US); Matthew R. Robinson, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/848,949

(22) Filed: May 3, 2001

(65) Prior Publication Data

US 2003/0055278 A1 Mar. 20, 2003

Related U.S. Application Data

(60) Provisional application No. 60/201,720, filed on May 3, 2000.

(51) Int. Cl.[7] .................. H05B 33/12; H05B 33/14; C07C 255/50; C07C 211/44
(52) U.S. Cl. .................. 428/690; 428/917; 313/503; 313/504; 313/506; 252/301.16; 558/411; 564/305
(58) Field of Search ................. 428/690, 917; 313/504, 505, 503; 252/301.16; 564/305; 585/25; 556/465; 558/411

(56) References Cited

U.S. PATENT DOCUMENTS 5,512,654 A    4/1996   Holmes et al.
6,444,333 B1 *  9/2002  Okada et al. ............... 428/690

FOREIGN PATENT DOCUMENTS

EP    WO 00/03565    *  1/2000
GB        2303633        2/1997

OTHER PUBLICATIONS

Warren J. Oldham et al., "Synthesis, Spectroscopy and Morphology of Tetrastilbenoidmethanes", J. American Chemical Society, 1998, 120, pp. 2987–2988.*

Wang et al., "Synthesis, Morphology and Optical Properties of Tetrahedral Oligo(phenylenevinylene) Materials", J. of American Chemical Society, 2000, 122, 5695–5709.*

* cited by examiner

Primary Examiner—Rena Dye
Assistant Examiner—Camie S Thompson
(74) Attorney, Agent, or Firm—Fulbright & Jaworski

(57) ABSTRACT

Electroluminescent compounds, devices and methods for making the foregoing are disclosed, which employ a novel topological strategy for designing amorphous molecular solids suitable for forming thin films in optoelectronic devices. In this approach chromophores are attached to a tetrahdral point of convergence.

10 Claims, 11 Drawing Sheets

SOLUBLE TETRAHEDRAL COMPOUNDS FOR USE IN ELECTROLUMINESCENT DEVICES

CROSS REFERENCE TO RELATED APPLICATIONS

This application claims the benefit of Provisional Patent Application No. 60/201,720, filed May 3, 2000, which is incorporated herein by reference.

STATEMENT REGARDING FEDERALLY FUNDED RESEARCH OR DEVELOPMENT

This invention was made with Government support under Grant Nos. DMR 9500627 and DMR 9632716, awarded by the National Science Foundation. The Government has certain rights in this invention.

BACKGROUND

The notion that π-conjugated organic materials should possess interesting and useful electronic properties analogous to conventional inorganic semiconductors such as silicon or gallium arsenide is now well established in the scientific literature.[1,2] Many of these expectations have been realized with the practical demonstration of electronic devices in which conjugated organic materials are responsible for charge transport and/or light generation. Examples include polymer or small molecule light-emitting diodes (LEDs)[3,4,5], photovoltaic devices[6] and field-effect transistors.[7,8] The prospect of realizing electrically driven organic lasers is also under intense investigation.[9] Much of the motivation for studying organic materials stems from the potential to tailor desirable optoelectronic properties and processing characteristics by manipulation of the primary chemical structure. Strategies for raising or lowering the highest occupied molecular orbit (HOMO) and lowest unoccupied molecular orbit (LUMO) levels include conjugation length control, as well as the introduction of electron donating or withdrawing groups to the parent chromophore.[10] Regulating the HOMO and LUMO energy levels permits fine tuning of charge injection properties. In emissive devices, the HOMO/LUMO energy difference directly controls emission frequency. Organic materials also offer the opportunity to adjust optical properties by taking advantage of processes unique to the excited state, i.e. excimer and exciplex formation.[11]

Several classes of luminescent polymers have been disclosed in the art heretofore. These include, for example, poly[1,4-phenylene vinylene], PPV[12], soluble derivatives of PPV, such as MEH-PPV[13], Aryl-substituted-PPV[14], and PPV copolymers[15]. Soluble derivatives of polythiophene are also known in the art, for example the poly(3-alkylthiophenes)[16]. The photoluminescent spectra of these polymers typically fall in the visible spectral region with colors ranging from green to red. Considerable progress has been made toward using these materials in light emitting displays with lifetimes sufficient for commercial products[17].

Low molar mass organic molecules can also be used for electroluminescent (EL) applications[18]. Disadvantages of these materials include their propensity for crystallization and difficulties in obtaining films by solution processing.

It is generally appreciated that the morphology of organic films plays a fundamental role in defining the functional characteristics of the material. However, studies that clearly relate electroluminescence and charge transport properties with molecular morphology remain scarce. The tendency of many small molecules to spontaneously crystallize[19] presents a limitation for LED applications because crystal formation destroys film homogeneity and crystal boundaries raise the resistance of the sample, eventually leading to electric shorting.[20]

The thermal stability of amorphous molecular solids as measured by the glass transition temperature has been shown to directly correlate with electroluminescence stability.[21] It has been argued that in some cases thermal cycling of an organic LED heterostructure device above the glass transition temperature causes degradation resulting from disruption of the organic-organic interface rather than crystallization.[22] It is proposed based on X-ray specular reflectivity data that large thermal expansion of one of the components associated with its glass transition causes catastrophic strain release at the hetero-interface between materials.

For transistor applications proper alignment of chromophores is desired because it enhances charge transport.[23] On the other hand, in the case of polymer LEDs, ordered regions result in strong interchain coupling and lower emission quantum yields.[24] Despite the obvious need to control the final arrangement of individual molecules in the bulk a priori, a detailed understanding of the relationship between chemical structure of a given organic material with the resulting morphology is still lacking.

Strategies to minimize interchain contacts in conjugated polymers have generally implemented the use of bulky sidegroups on the polymer backbone. These attachments improve solubility by limiting interchain contacts but are typically aliphatic in nature and therefore limit charge injection and migration across the solid sample.[25] In response to these limitations, considerable efforts have been dedicated to developing molecules of intermediate molecular weight that minimize the aliphatic content and at the same time resist crystallization. Molecular shape is an important parameter in these efforts. Some of the recent strategies rely on creating molecular shapes that, from an intuitive perspective, can be considered "awkward" to packing. Examples include "starburst", dendritic, tetrahedral, and spiro shaped molecules, as shown below.[26]

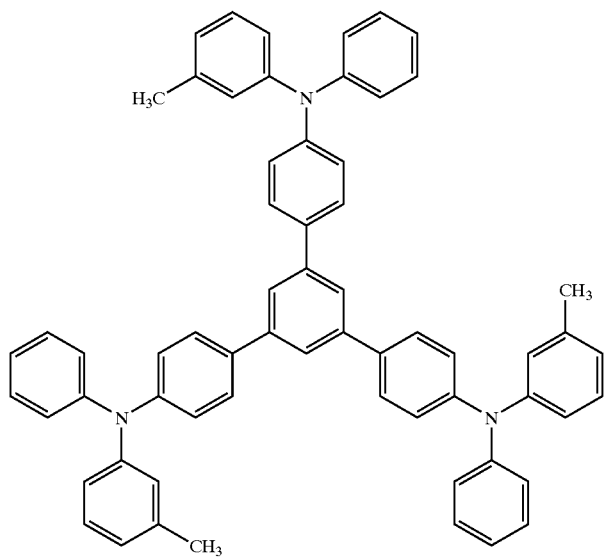
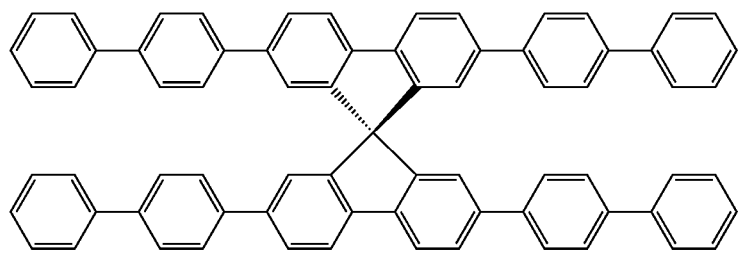
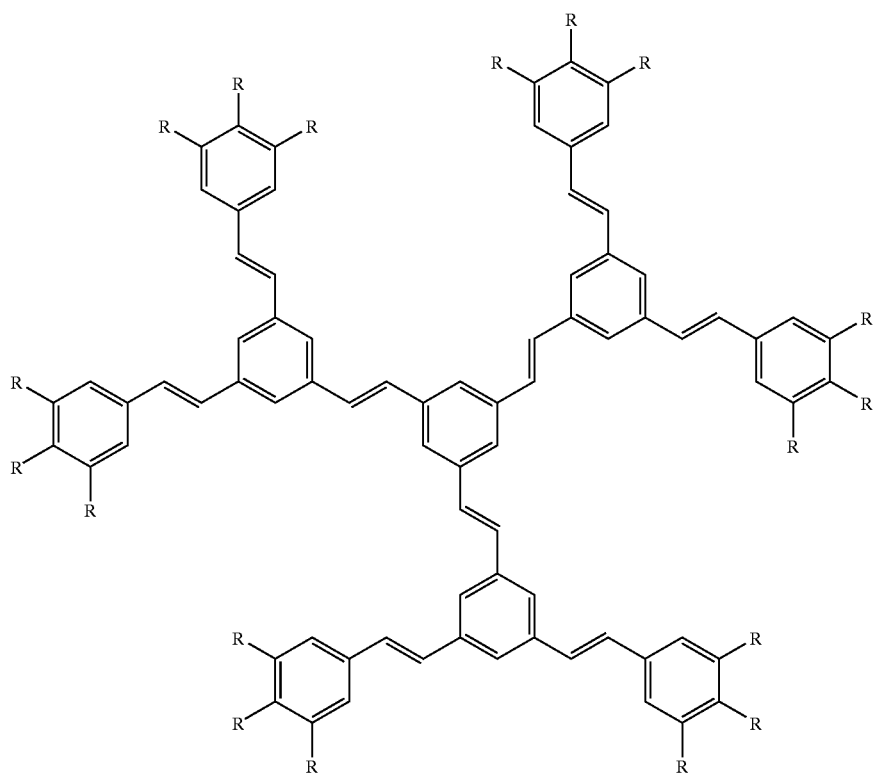

-continued

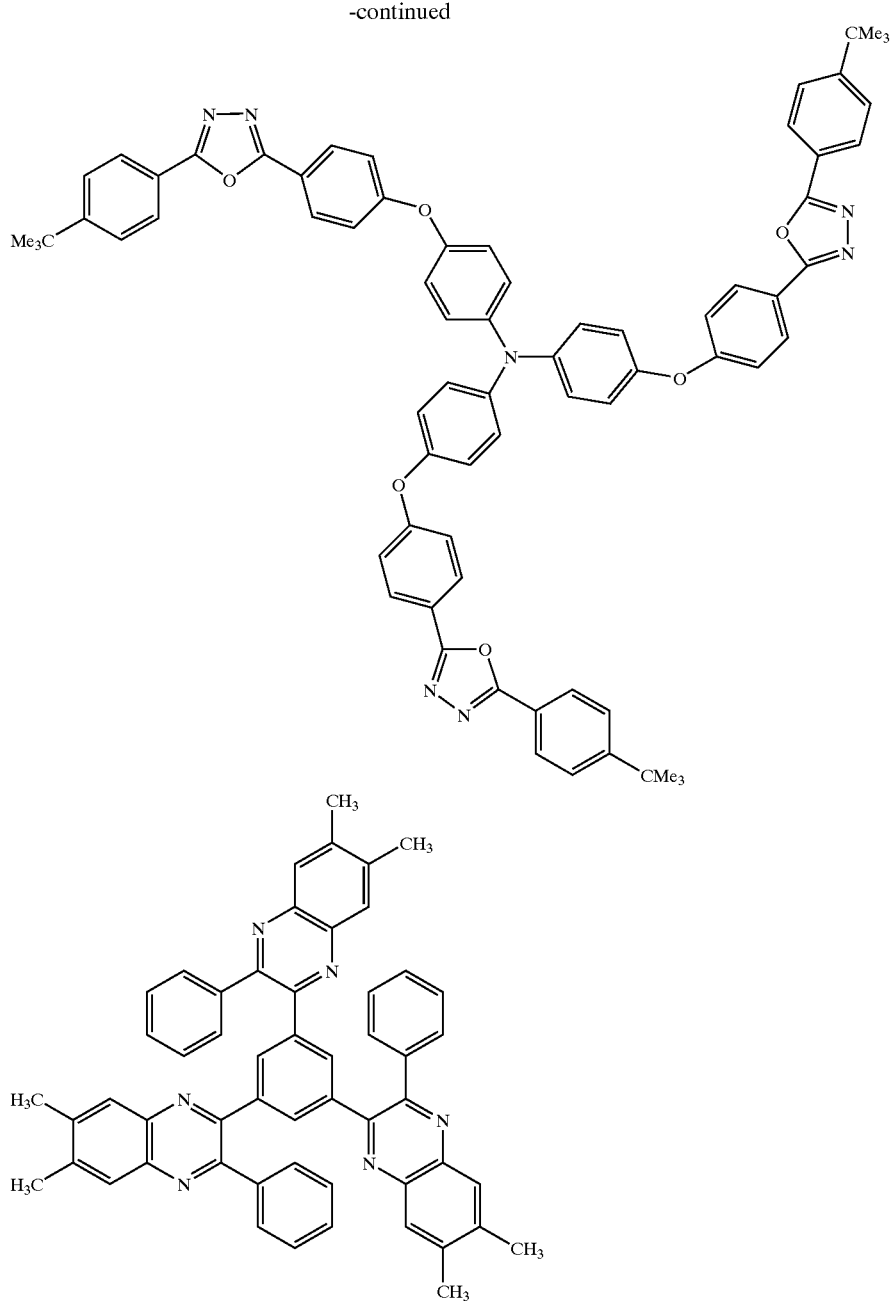

Solution processing methods can be employed with these materials to yield kinetically trapped, amorphous solids that resist crystallization. Furthermore, these materials show elevated glass transition temperatures despite their modest molecular dimensions. Molecules such as the cues above embody all of the beneficial properties of small molecules, namely purity and well-defined structure, combined with the ability to cast thermally robust films directly from solution, a property characteristic of polymeric materials.

The use of semiconducting (conjugated) polymers and oligomers as EL materials in light emitting displays offer a number of advantages, including high brightness at low operating voltage, low weight, thin profile and low power consumption over conventional display elements such as incandescent lamps and liquid crystal displays. The relatively simple processing enabled by the use of soluble semiconducting polymers provides a pathway to low cost, high volume fabrication.

Accordingly, there is intense interest in developing improved organic EL materials of intermediate dimensions with topological attributes that discourage crystallization. Few guidelines are available for this purpose and new general structures that combine a preference to form useful films with the electrooptical requirements for EL are needed for the fabrication of more efficient LEDs.

SUMMARY OF THE INVENTION

The present invention is directed to a novel class of tetrahedral compounds that satisfy the need for improved organic materials that are luminescent, electroluminescent, and emit visible light with high photoluminescence efficiency. Moreover these materials are thermally stable, resist crystallization, soluble in common organic solvents and can be cast into films for use in electroluminescent devices.

The soluble tetrahedral compounds of the present invention are of general formula (I), where R1, R2, R3 and R4 are optoelectronic arms, generally comprised of organic electrochromophores, which are similar or independent of each other, and TS is a tetrahedral junction unit.

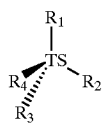

(I)

The tetrahedral junction unit, TS, includes but is not limited to tetraphenylmethane, tetraphenylsilane, sp$^3$ hybridized C or Si atoms, tetraphenyladamantane, adamantane and cubane.

R1, R2, R3 and R4 can be different or the same and are optoelectronic arms corresponding to conjugated monomers, oligomers, polymers, copolymers or other organic electrochromophores that are used in EL applications.

Particular preference is given to R1, R2, R3 and R4 corresponding to general formulas (II) or (III):

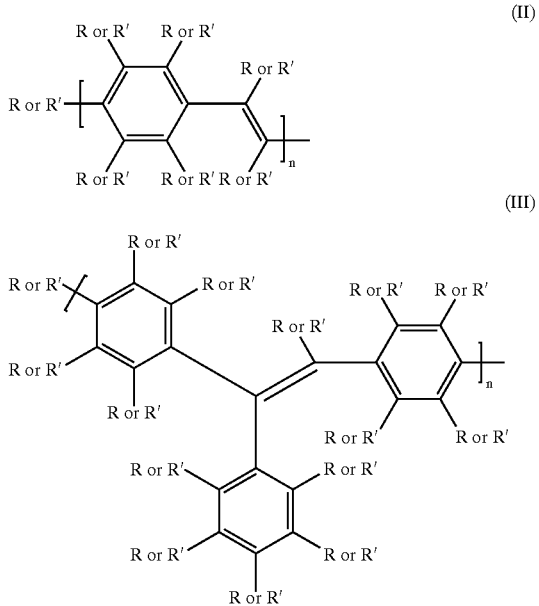

wherein the symbols have the following meaning:
R=H;
R'=alkoxy, alkyl aryl, aryloxy, cyano, halide, amido or other analogous functionalities that influence morphology and electrooptical properties; and
n=1–100

Preferred versions of general formula (II) have n values greater than 2.

The present invention also includes a method of making a tetrahedral compound having one or more organic chromophore arms attached to a tetrahedral junction site. This method includes the steps of providing a tetrahedral junction molecule having four reactive functionalities and reacting one or more of the reactive functionalities with one or more organic chromophores, each chromophore having a single complementary functionality that reacts with one of the reactive functionalites, thereby forming a bond to the tetrahedral junction molecule.

The present invention also includes improved thin film devices in an anode-semiconductor-cathode configuration, wherein the semiconductor is a thin film of the tetrahedral compound. The efficiency of the device may be improved by including a hole or electron transport agent with the tetrahedral compound, as a composition or as a separate charge transport layer. Preferred versions of the device include at least two layers consisting of an electroluminescent layer, an electron transport layer, and/or a hole transport layer, where at least one of the layers contains the tetrahedral compound of the present invention.

BRIEF DESCRIPTION OF THE DRAWINGS

These and other features aspects, and advantages of the present invention will become better understood with respect to the following description and accompanying drawings where.

DETAILED DESCRIPTION

Overview

Figure 1:
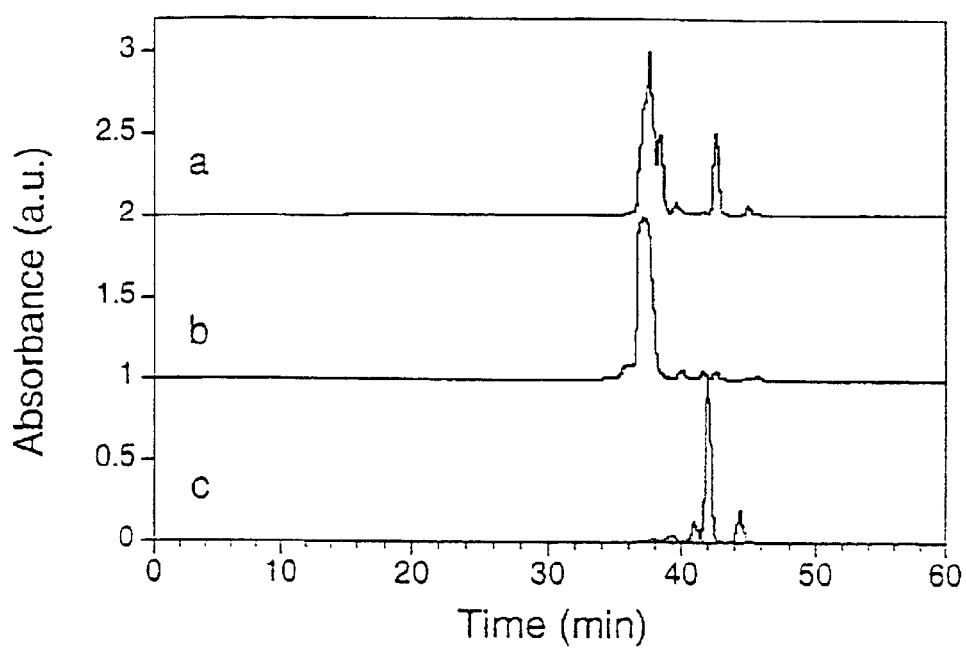
FIG. 1 shows SEC analysis of crude product mixture of C(DPVBi)$_4$ obtained using (a) Pd(PPh$_3$)$_4$, (b) Pd(dppf)Cl$_2$, and (c) Herrmann's catalyst, A as Suzuki coupling catalysts, respectively.

The present disclosure outlines the generality of the tetrahedral approach for designing amorphous optoelectronic organic materials.[27] Complete synthetic details are presented for a range of tetrahedral junction sites and chromophore "arms" of different structure and conjugation length. We then compare the optical properties observed in fluid solution with those of the amorphous thin films. These data give insight into the extent of chromophore/chromophore interactions in the solid state and the potential utility of these materials in optoelectronic devices.

The soluble tetrahedral compounds of the present invention are of general formula (I), where R1, R2, R3 and R4 are optoelectronic arms or organic electrochromophores and are similar or independent of each other, and TS is a tetrahedral junction unit.

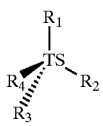
(I)

The tetrahedral junction unit, TS includes but is not limited to tetraphenylmethane, tetraphenylsilane, sp$^3$ hybridized C or Si atoms, tetraphenyladamantane, adamantane and cubane.

R1, R2, R3 and R4 can be different or the same and are optoelectronic arms corresponding to conjugated monomers, oligomer, polymers, copolymers or other organic electrochromophores that are used in EL applications.

Particular preference is given to R1, R2, R3 and R4 corresponding to repeating monomeric units having at least one of the following general formulas:

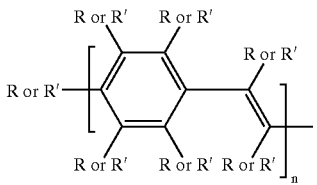
II

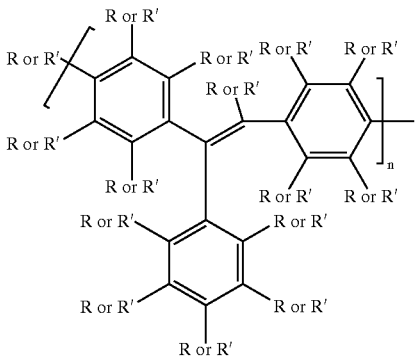
III

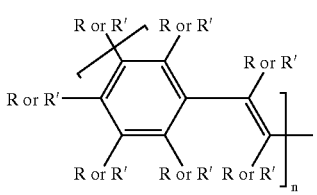
IV

-continued

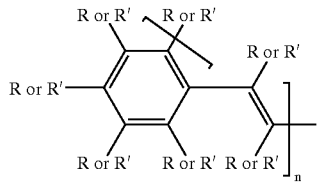
V

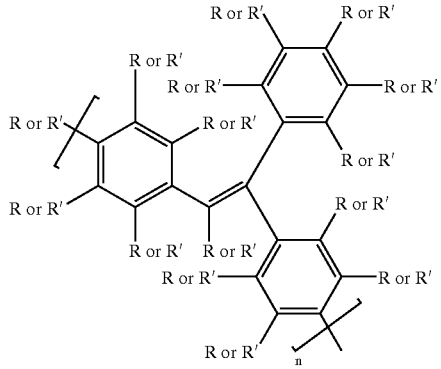
VI

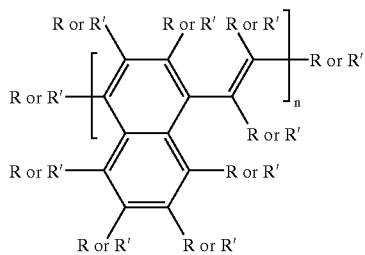
VII

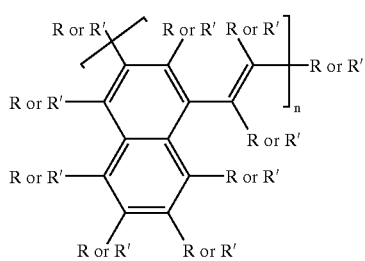
VIII

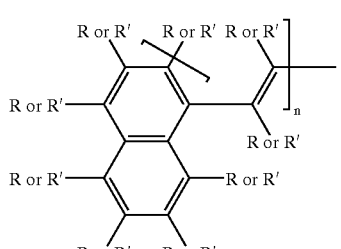
IX

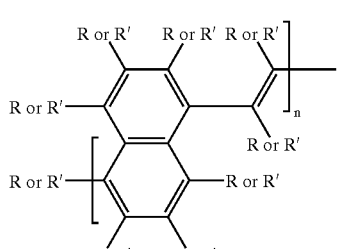
X

-continued
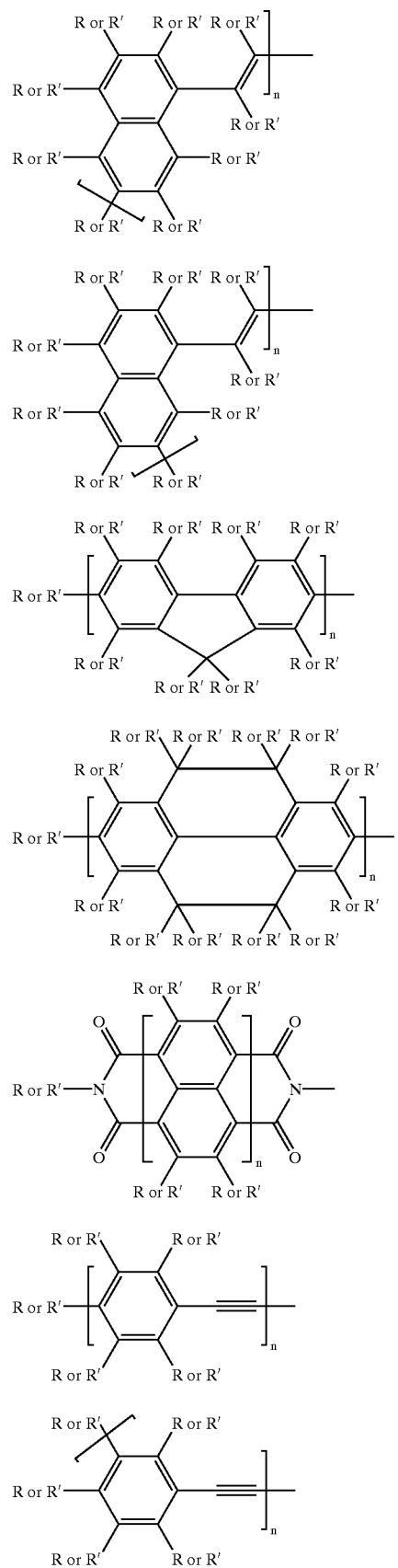
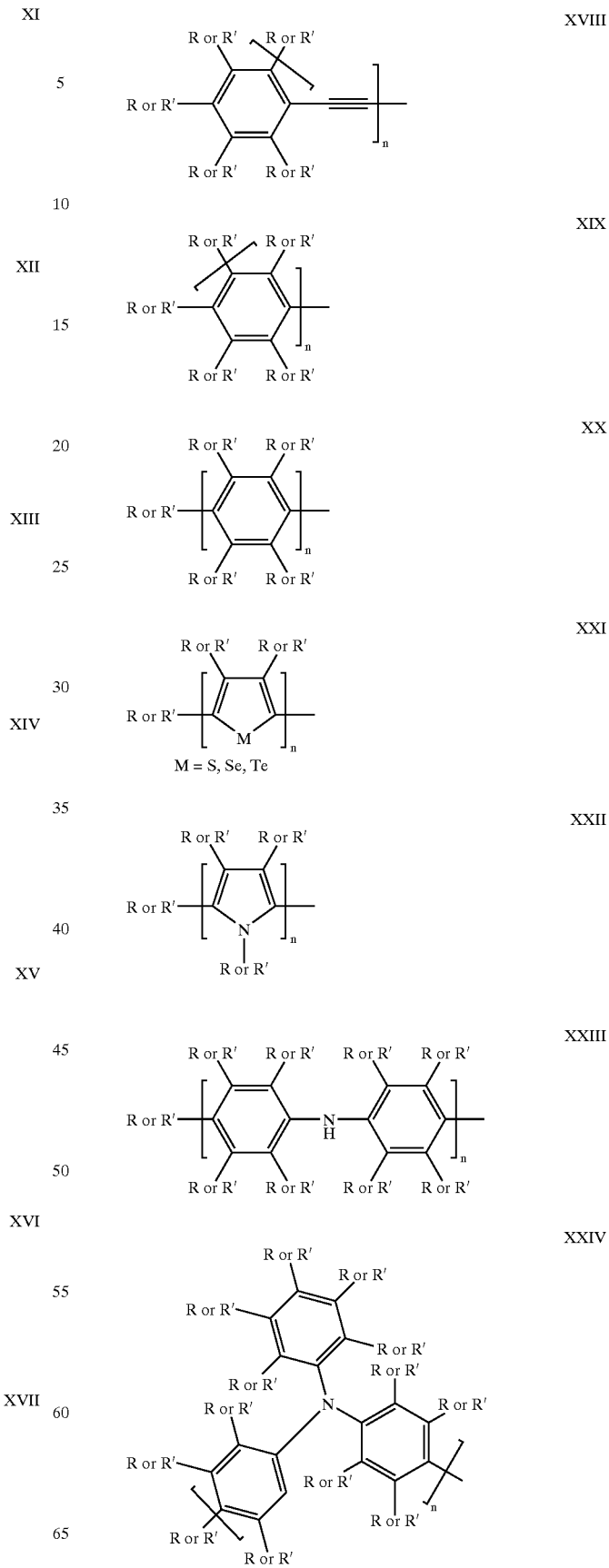

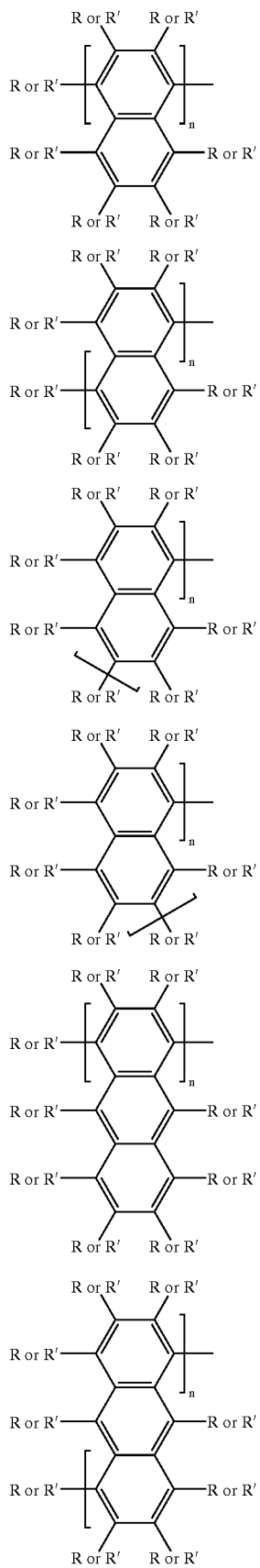
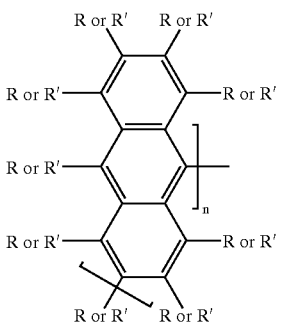
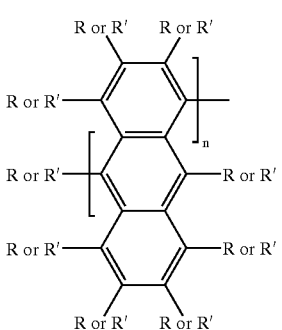
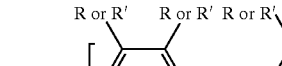

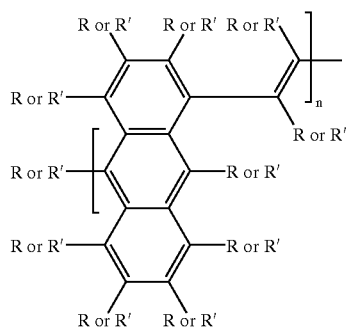
XXXVI
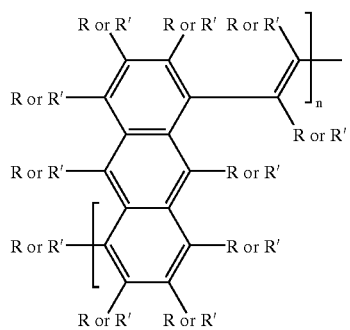
XXXVII
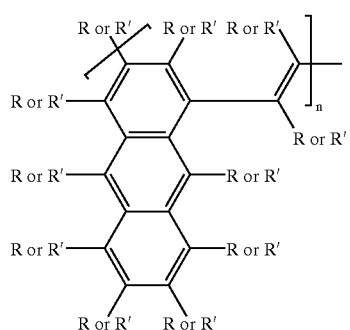
XXXVIII
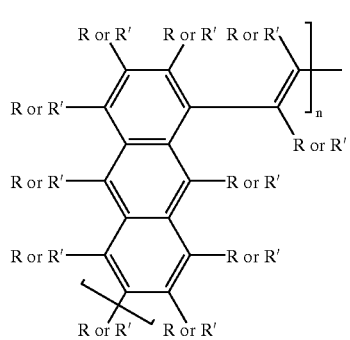
XXXIX
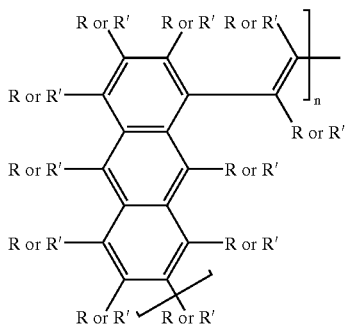
XL
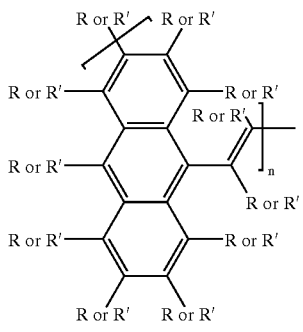
XLI
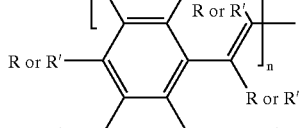
XLII
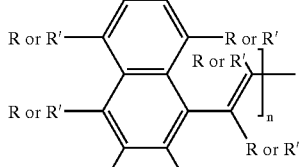
XLIII
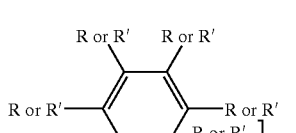
XLIV

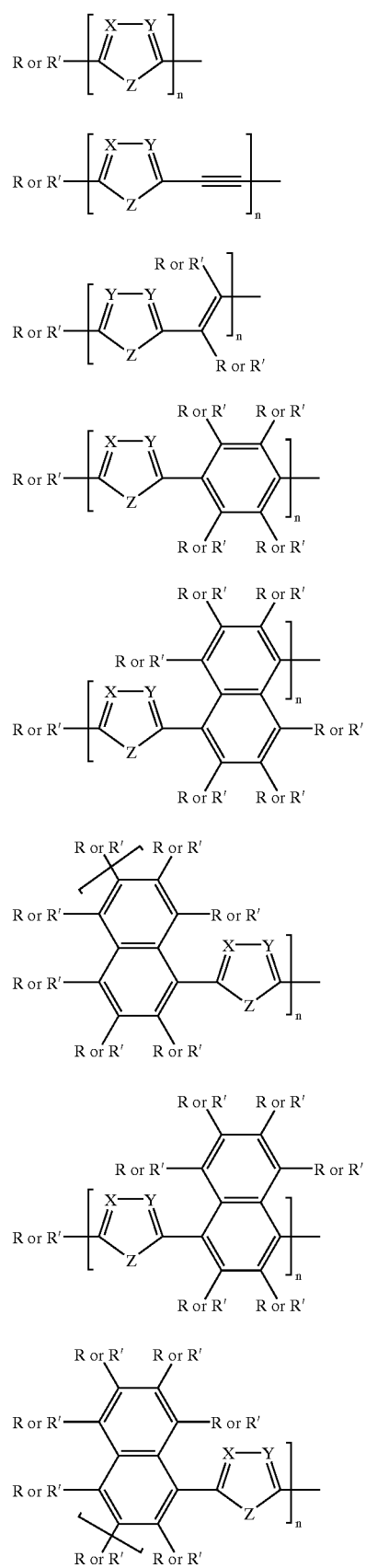
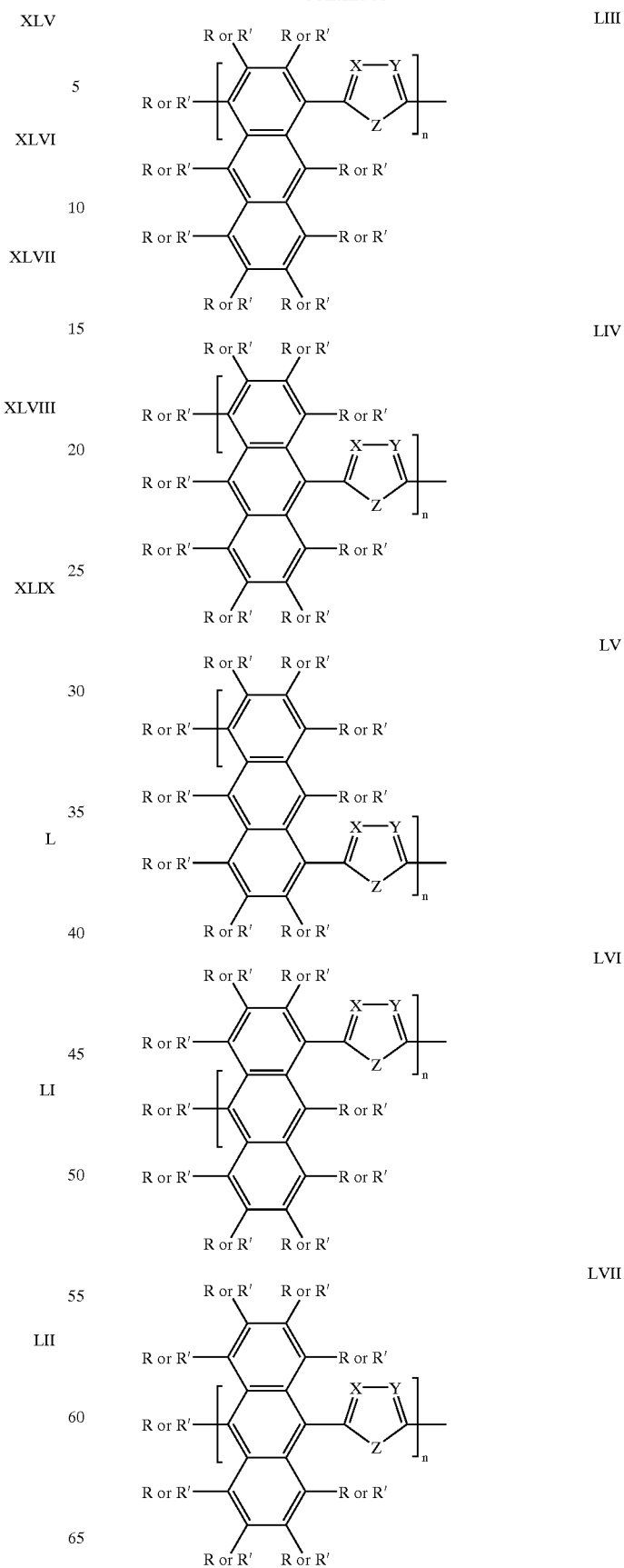

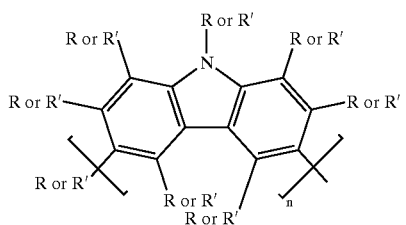

LVIII

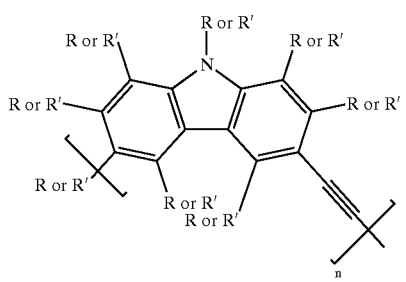

LIX

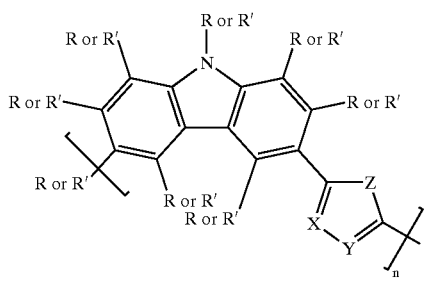

LX

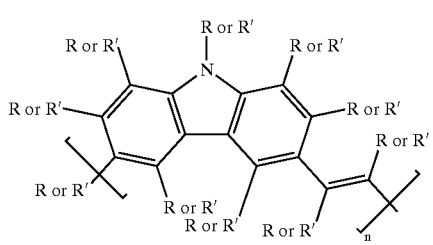

LXI

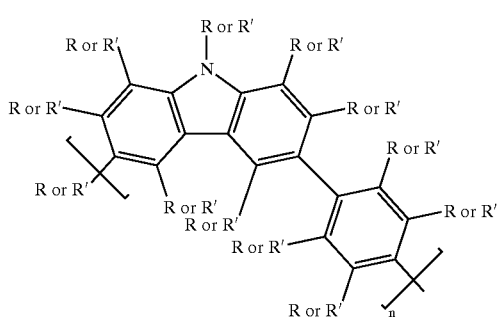

LXII

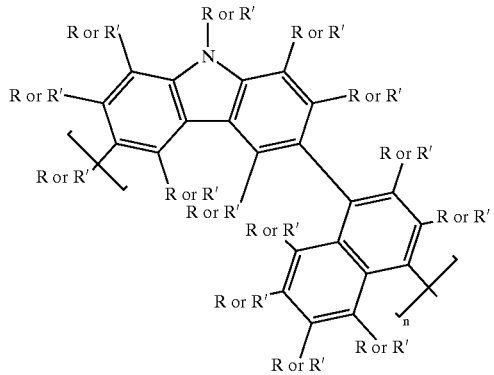

LXIII

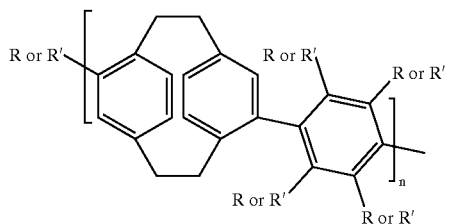

LXIV

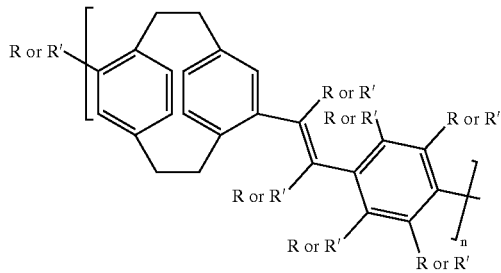

LXV

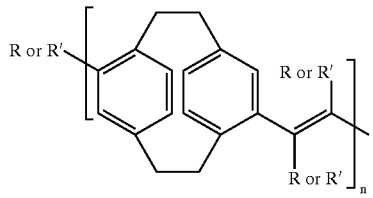

LXVI wherein R=H; R'=alkoxy, alkyl, aryl, aryloxy, cyano, halide, amido or other analogous functionalities that influence morphology and electrooptical properties; and n=1–100. X, Y are identical or different and are C—R', CR, NR, NR' and Z is OR, OR', SR, SR', NR, NR', CRR', —CH=CH—R, —CH=CH—R', CN.

Monomeric units composed of combinations from the above repeat units, as well as stereochemical relationships are also considered to be within the scope of the present invention.

In one preferred version of the tetrahedral compound, TS is selected from the group consisting of tetraphenylmethane, tetraphenylsilane, an sp³ hybridized silicon atom, tetraphenyladamantane, adamantane and cubane; R1, R2, R3 and R4 are each optoelectronic arms corresponding to general formula II, wherein R is hydrogen; R' is alkoxy, alkyl, aryl, aryloxy, cyano, halide, or amino; and n is an integer from 2 to 100. More preferably, n is at least about 3. In another preferred version of the tetrahedral compound, TS is selected from the group consisting of tetraphenylmethane, tetraphenylsilane, an sp³ hybridized carbon or silicon atom, tetraphenyladamantane, adamantane and cubane; R1, R2, R3 and R4 are each optoelectronic arms corresponding to general formula III, wherein R is hydrogen; R' is alkoxy alkyl, aryl, aryloxy, cyano, halide or amino; and n is an integer from 1 to 100.

Compounds of formula (I) having good solubilities in common organic solvents, which resist crystallization and can be cast into films directly from solution are preferred. These properties enable the fabrication of organic electroluminescent devices.

In addition, preferred versions of the tetrahedral compounds are luminescent, electroluminescent, and/or emit visible light, the color of which is controlled by the molecular structure and molecular weight of the optoelectronic arms of the compound. In particularly preferred versions the tetahedral compounds of the present invention can provide an emissive film for use in blue-emitting electroluminescent devices.

The criteria for selecting a conjugated monomer, oligomer, polymer or copolymer for use in high efficiency, stable light emitting devices include the following:

(a) In an efficient luminescent polymer medium, radiative recombination is favored over non-radiative recombination. PL efficiencies in excess of 10% are preferred; PL efficiencies in excess of 25% are still more preferred; and PL efficiencies in excess of 50% are still more preferred.

(b) Emissive polymers or oligomers which form high quality pin-hole free films by processing from solution, for example by spin-casting, are preferred.

(c) To ensure good thermal stability, the polymer should be designed to have a high glass transition temperature ($T_g$).

(d) High efficiency light emitting diodes (LEDs) require balanced carrier injection and transport. Ideally, the injection of holes at the anode and electrons at the cathode should be equal and the transport mobility of electrons and holes in the polymer should be equal.

Synthesis of Soluble Tetrahedral Tetramers

The present invention includes a method of making a tetrahedral compound having one or more organic chromophores attached to a tetrahedral junction site. This method includes the steps of providing a tetrahedral junction molecule having four reactive functionalities and reacting one or more of the reactive functionalities with one or more organic chromophores, each chromophore having a single complementary functionality which reacts with one of the reactive functionalities of the tetrahedral molecule to form a bond. Preferred reactive and complementary functionalities include, but are not limited to aryl halides, olefins, acetylenes, boronic esters, and carbonyls.

Tetrahedral junction molecules having four reactive functionalities can be prepared, for example, starting with a tetrahalogenation of the tetraphenylmethane, tetraphenylsilane, tetraphenyladamantane in the 4 positions (Su, D.; Menger, F. M. *Tett. Lett.* 1997, 38, 1485–1488 and Mathias, L. J.; Reichert, V. R.; Muir, A. V. G. *Chem. Mater.* 1993, 5, 4–5) and a subsequent functionalization reaction.

In preferred versions of the present invention, chromophore "arms," can be covalently linked to tetraphenylmethane, tetraphenyladamantane, or tetraphenylsilane cores using palladium catalyzed coupling methodology. Thus, reaction of tetrahedral junction compounds having reactive aryl halide functionalities, e.g., $E(C_6H_5X)_4$ (E=C and adamantane, X=I; E=Si, X=Br), with styrene derivatives having complementary olefin functionalities under Heck coupling conditions yields the corresponding tetrakis(stilbenyl) compounds.

The simple stilbenyl-derivatives were found by DSC measurements and powder diffraction experiments to be crystalline compounds. Moreover, comparison of single crystal x-ray diffraction data shows that $C(STB)_4$ and $Si(STB)_4$ form isomorphous crystals. Accordingly, tetrahedral compounds with more extended conjugation, which can resist crystallization are preferred. Thus, in one preferred embodiment, reaction of excess 1-(4'-tert-butylstyryl)-4-(4'-vinylstyryl)benzene with $C(C_6H_4I)_4$ provides tetrakis(4-(4'-(4"-tert-butylstyryl)styryl)stilbenyl)methane ($C(4R—{}^tBu)_4$) in low yield (~20%). In another embodiment, the more soluble analog, tetrakis(4-(4'-(3", 5"-di-tert-butylstyryl)styryl)stilbenyl)methane ($C(4R—2^tBu)_4$) is prepared similarly using 1-(3'5'-di-tert-butylstyryl)-4-(4'-vinylstyryl)benzene and in better yield (~80%). Alkoxy substituents can also be used to increase solubility. For example, tetrakis((4-(2'5'-dioctoxy-4'-styryl)styryl)stilbenyl)methane, T—4R—$OC_8H_{17}$, was prepared by treatment of $C(C_6H_4I)_4$ with excess 2,5-dioctoxy-1-styryl-4-(4'-vinylstyryl)benzene (yield ~73%).

In another version of the present invention, triphenylethylene derivatives having complementary boronic ester functionalities are reacted with tetrahedral junction compounds having reactive aryl halide functionalities. Thus, reaction of 1,1-diphenyl-2-(4-dihydroxyboronphenyl)-ethene or 2-(4-pinacolatoboronphenyl)-3,3-diphenylacrylonitrile with tetrakis(4-bromophenyl)methane using Suzuki coupling methodology gives tetrakis(4,4'-(2,2-diphenyl-vinyl)-1,1'-biphenyl)-methane ($C(DPVBi)_4$) or tetrakis(4,4'-(3,3-diphenylacrylonitrile)-1,1'-biphenyl)methane ($C(DPAB)_4$), respectively, in good yields.

Synthesis of Carbon-Centered Tetramers

The four ring tetramer tetrakis(4-(4'-(4"-tert-butylstyryl)styryl)stilbenyl)methane ($C(4R—{}^tBu)_4$) was synthesized as shown in Scheme 1. The requisite 1-(4'-tert-butylstyryl)-4-(4'-vinylstyryl)benzene can be obtained readily by olefination of 4-(4'-vinylstyryl)benzaldehyde using (4-tert-butyl) benzyltriphenylphosphonium bromide. Four equivalents of 1-(4'-tert-butylstyryl)-4-(4'-vinylstyryl)benzene react with $C(C_6H_4I)_4$ to give $C(4R—{}^tBu)_4$, albeit in only ~20% yield. We suspect that the low yield of the reaction is due to the poor solubility of partly coupled intermediates.

Scheme 1

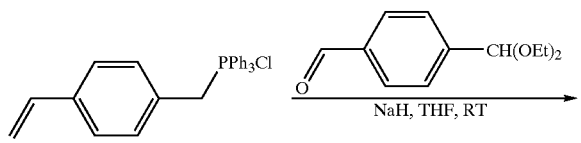

-continued

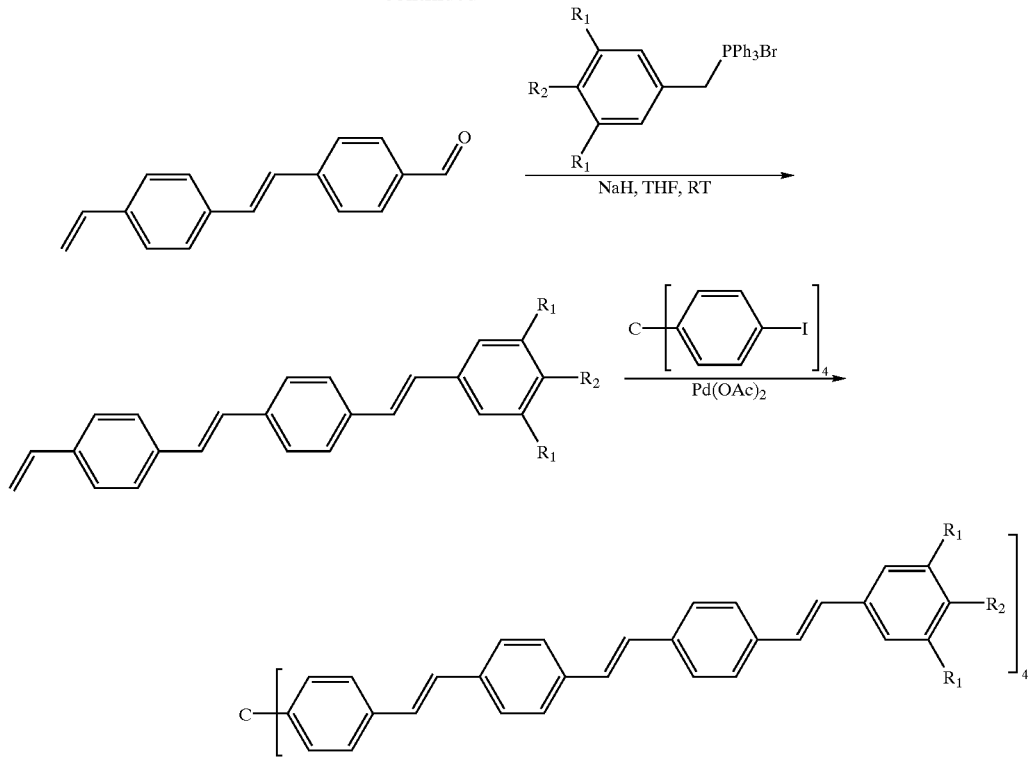

C(4R—$^t$Bu)$_4$: R$_1$ = H, R$_2$ = $^t$Bu
C(4R—2$^t$Bu)$_4$: R$_1$ = $^t$Bu, R$_2$ = H

Improved solubility for processability and higher reaction yields were expected for tetrakis(4-(4'-(3", 5"-di-tert-butylstyryl)styryl)stilbenyl)methane (C(4R—2$^t$Bu)$_4$), by virtue of the eight tert-butyl groups around the periphery of the molecule, and this molecule was prepared as shown in Scheme 1. Coupling of 1-(3'5'-di-tert-butylstyryl)-4-(4'-vinylstyryl)benzene with C(C$_6$H$_4$I)$_4$ under phase transfer conditions affords C(4R—2$^t$Bu)$_4$ in 80% yield. For both C(4R—$^t$BU)$_4$ and C(4R—2$^t$BU)$_4$, the products are obtained as a mixture of isomers which can be converted to the all-trans isomers by irradiation using a mercury lamp.

As shown in Scheme 2, the reaction of tetrakis(4-iodophenyl)methane with excess 2,5-dioctyloxy-1-styryl-4-(4'-vinylstyryl)benzene (3) under palladium-catalyzed Heck coupling[28] conditions affords tetrakis((4-(2'5'-dioctyloxy-4'styryl)styryl)stilbenylmethane (T—4R—OC$_8$H$_{17}$) in 72% yield.[29] The olefin 3 is prepared by reaction of 2,5-dioctyloxy-4-(4'-vinyl)styrylbenzaldehyde (2) and benzyltriphenylphosphonium bromide with an 82% yield. Olefin 2 is prepared according to literature precedent.[30] T—4R—OC$_8$H$_{17}$ is initially obtained as a mixture of cis-trans isomers which can be converted to the all-trans isomer by irradiation with a mercury lamp.

Scheme 2

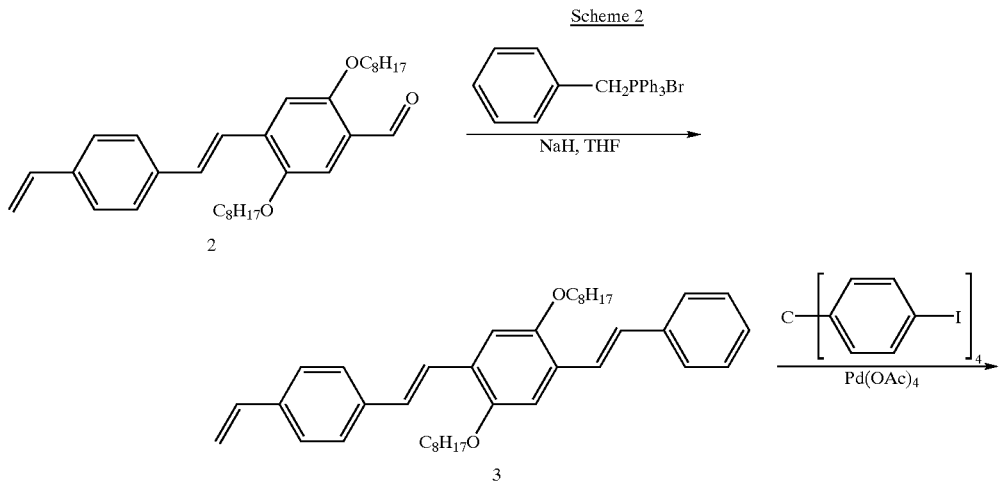

-continued

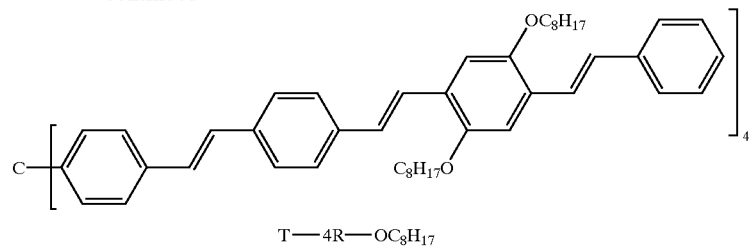

T—4R—OC$_8$H$_{17}$

Tetrakis(4-(4'-(3", 5"-dihexyloxystyryl)styryl)stilbenyl)methane (T—4R—OC$_6$H$_{13}$) is prepared similarly from excess 1-vinyl-4-(3'5'-dihexyloxystyryl)stilbene (4) and tetrakis(4-iodophenyl)methane (Scheme 3). The olefin 4 is easily prepared by consecutive Wittig reactions on singly protected 1,4-terephthaldehyde in 80% yield. Irradiation of degassed benzene solutions affords the all-trans isomer.

Interestingly, this stilbenoid chromophore gives very weak photoluminescence in fluid solution. We attribute the marked difference in fluorescence efficiency between solution and solid phase experiments to conformationally controlled radiationless transitions that are typical of trans-stilbenes.[32] Amorphous films of DPVBi fabricated by vacuum evaporation have a tendency to crystallize. For example, when investigated by differential scanning calorimetry, we have found that frozen glasses formed by rapidly quenching a melted sample of DPVBi with liquid nitrogen, undergo a glass transition at 64° C., then crystallize at 106° C. (ΔT=10° C./min). The promising electroluminescent properties of DPVBi make it an ideal candidate to integrate within a tetrahedral structure to change its bulk morphology.

Scheme 3

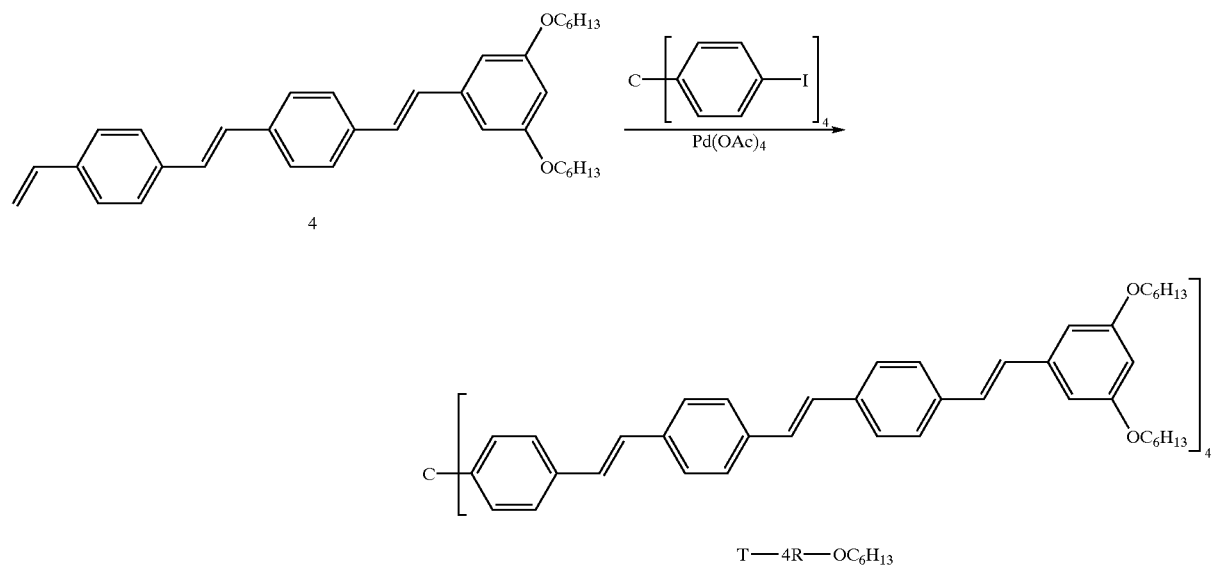

T—4R—OC$_6$H$_{13}$

Triphenylethene Derivatives

Efficient blue organic LEDs have recently been constructed using the active material, 4,4'-bis(2,2-diphenylvinyl)-1,1'-biphenyl (DPVBi) to function as both the electron transport and electroluminescence layer.[31] The active emitting material in these devices is characterized by high solid-state photoluminescence efficiency and is based on the triphenylethene chromophore.

DPVBi

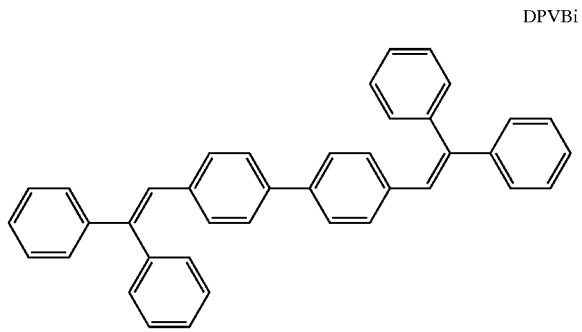

A suitably functionalized triphenylethene unit can be prepared in two steps. A Horner-Wadsworth-Emmons reaction between 4-bromobenzyl(diethylphosphonate) and benzophenone gives bromine substituted triphenylethene.[33] Treatment of this compound with n-BuLi and then reaction with B(Oi—Pr)$_3$, followed by aqueous workup, provides 1,1-diphenyl-2-(4-dihydroxyboronphenyl)-ethene (DDE).[34] Suzuki coupling[35] of the aromatic boron reagent and tetrakis (4-bromophenyl)methane (C(C$_6$H$_4$Br)$_4$) gives the desired target, tetrakis(4,4'-(2,2-diphenyl-vinyl)-1,1'-biphenyl)-methane (C(DPVBi)$_4$) (eq 1).

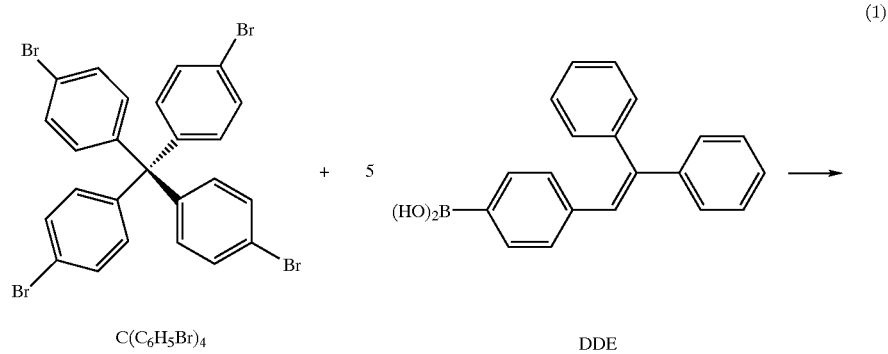

(1)

C(C₆H₅Br)₄    +   5   DDE   →

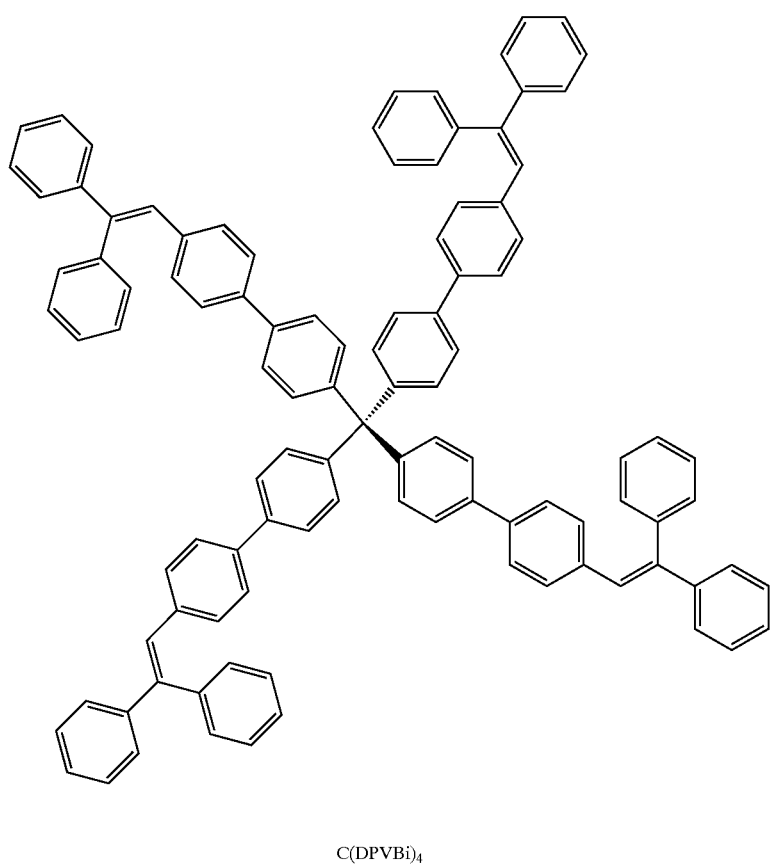

C(DPVBi)₄

Three different Suzuki coupling protocols were evaluated to optimize reaction yields.[36] A direct comparison of the reaction between DDE and C(C₆H₄Br)₄ using either Pd(PPh₃)₄ (4%) or Pd(dppf)Cl₂ (4%) as catalyst precursor was carried out. Both reactions were performed at the same reactant concentrations in THF at 75° C. using excess 2M NaHCO₃ as the base. The third protocol evaluated in eq 1 employed Hermann's catalyst (2%), a cyclometallated palladium catalyst, under the previously published[37] optimized coupling conditions with K₂CO₃ as base and ortho-xylene as solvent at 130° C. In each case a small aliquot of the crude product mixture was diluted with chloroform and the resulting homogeneous solution was then analyzed by size exclusion chromatography. As shown in FIG. 1b, the reaction catalyzed by Pd(dppf)Cl₂ results in complete conversion to the desired C(DPVBi)₄. SEC analysis of the reaction catalyzed with Pd(PPh₃)₄ shows a mixture of C(DPVBi)₄ and partially coupled products (FIG. 1a). Finally, the cyclometallated palladium catalyst, A was found to be completely inactive for these substrates (FIG. 1c).

Figure 2:
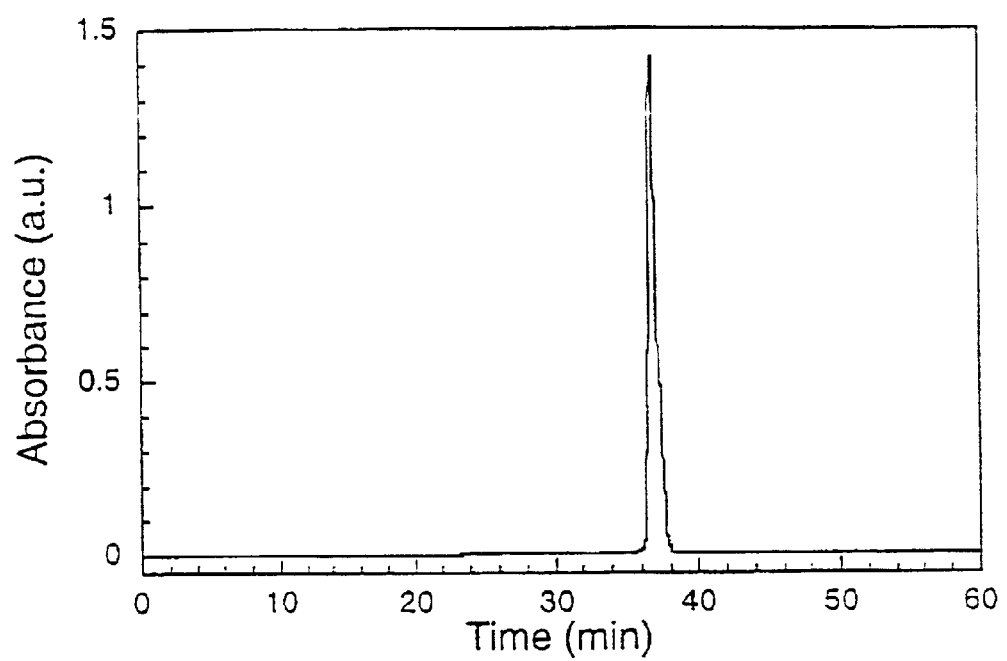
FIG. 2 shows SEC analysis of C(DPVBi)$_4$.

Optimized conditions using Pd(dppf)Cl₂ gives C(DPVBi)₄ in 82–86% yield following purification by flash chromatography (silica gel, hexanes/chloroform). The white powder can be re-crystallized upon diffusion of methanol into a chloroform solution. The fine crystalline needles thus obtained were too small for X-ray analysis. The SEC trace of the product demonstrates excellent purity (FIG. 2).

A related material was prepared in which the vinylic hydrogen of C(DPVBi)$_4$ is substituted with a cyano group. The stabilized LUMO of the cyano-substituted triphenylethene fragment (2,3,3-triphenylacrylonitrile) is expected to enhance electron injection and transport as is observed for CN-PPV.[38] Knovenagle condensation between 4-bromobenzonitrile and benzophenone gives 2-(4-bromophenyl)-3,3-diphenylacrylonitrile (Scheme 4). Metathesis of the bromine atom for boronpinacolate proceeds in good yield using the method of Miyaura.[39] In this case metathesis of bromine using the n-BuLi/B(OiPr)$_3$ protocol is not compatible with the sensitive cyano functionality. Five equivalents of 2-(4-pinacolatoboron-phenyl)-3,3-diphenylacrylonitrile react smoothly with tetrakis(4-bromophenyl)methane using the optimized Pd(dppf)Cl$_2$ catalyzed coupling conditions to yield tetrakis(4,4'-(3,3-diphenylacrylonitrile)-1,1'-biphenyl)methane, C(DPAB)$_4$ in 82% yield, following purification by flash chromatography. Compound C(DPAB)$_4$ has been fully characterized and the details can be found in the Examples.

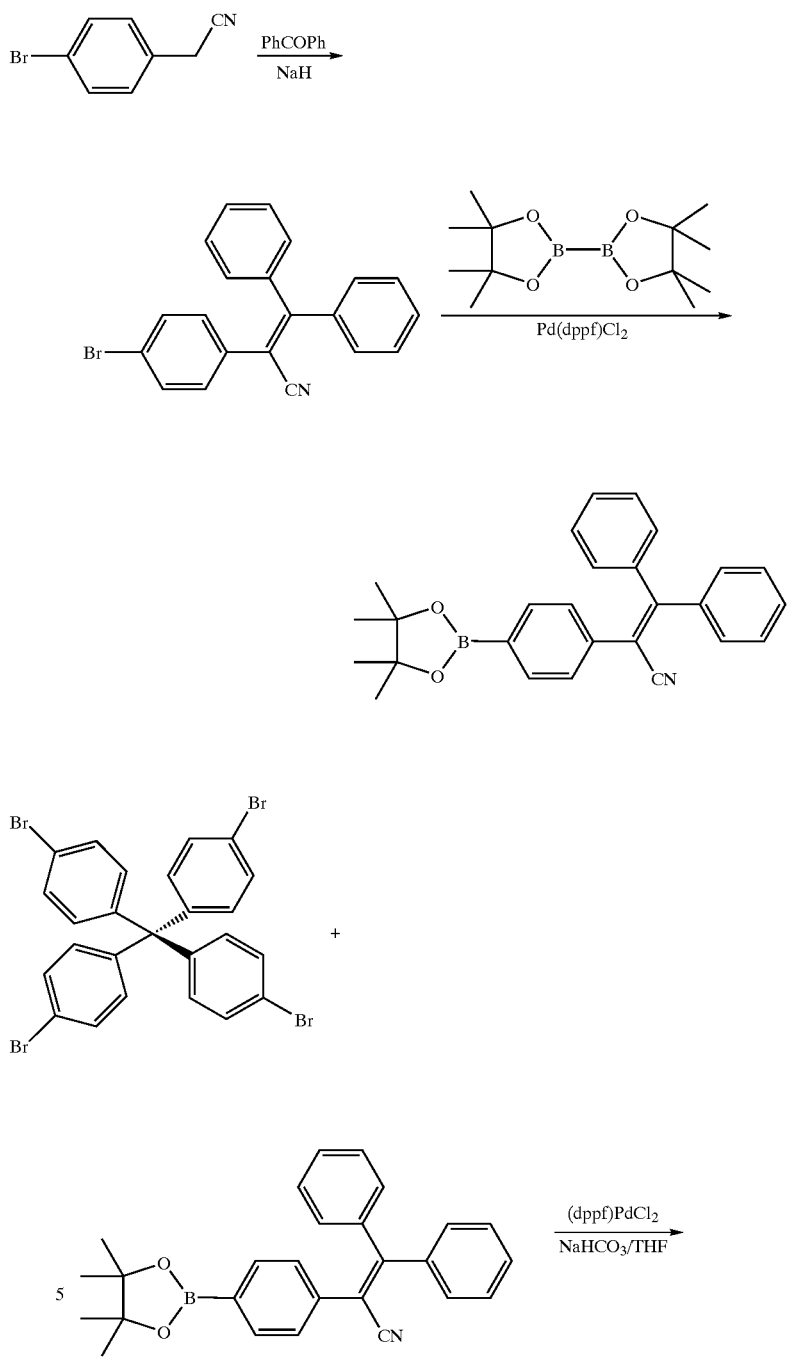

Scheme 4

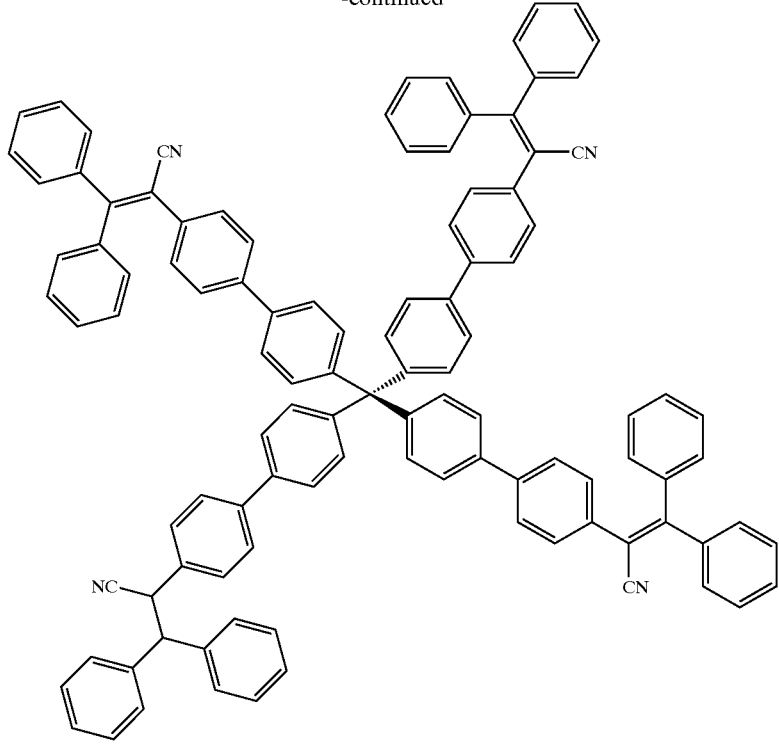

Adamantane and Silane Cores

In addition to the tetraphenylmethane core we chose to study tetrahedral shaped complexes linked by tetraphenyladamantane and tetraphenylsilane cores. These specific fragments were chosen because they are readily available using literature procedures, they are easily functionalized, and they maintain a rigid tetrahedral relationship between the radiating groups. Furthermore, comparison of the adamantane, methane, and silane cores allows one to probe the effect of core volume on the morpological properties.

Reaction of tetrakis(4-iodophenyl)adamantane (Ad($C_6H_4I$)$_4$)[40] with excess styrene under Heck conditions similar to Schemes 1–3 affords tetrastilbenyladamantane (Ad(STB)$_4$) in approximately 25% yield. The optimized reaction conditions described for the tetraphenylmethane core are transferable to the other cores so that discussion of the experimental procedures will be kept to a minimum for the new cores. Purification by precipitation of a hot benzene solution into methanol provides Ad(STB)$_4$ as a white powder. Palladium catalyzed coupling of Ad($C_6H_4I$)$_4$ with excess 4,4'-tert-butylvinylstilbene gives tetrakis(4-tert-butylstyrylstilbenyl)adamantane (Ad($^t$BuSSB)$_4$). In this case we find little difference in final yield between the phase transfer conditions (28%) and the use of Hermann's catalyst, (31%).

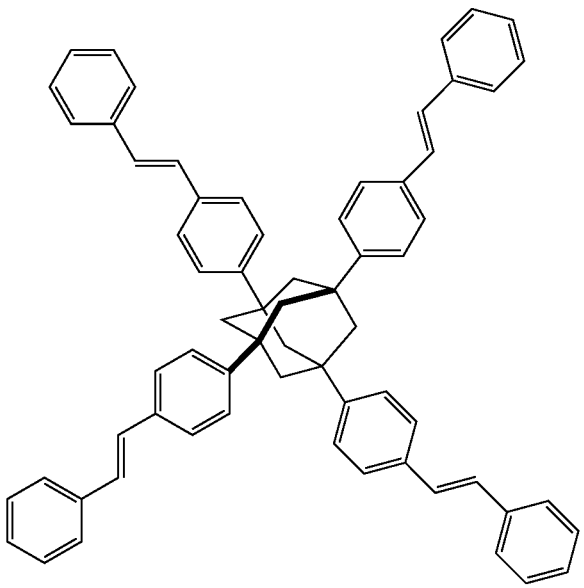

Ad(STB)$_4$

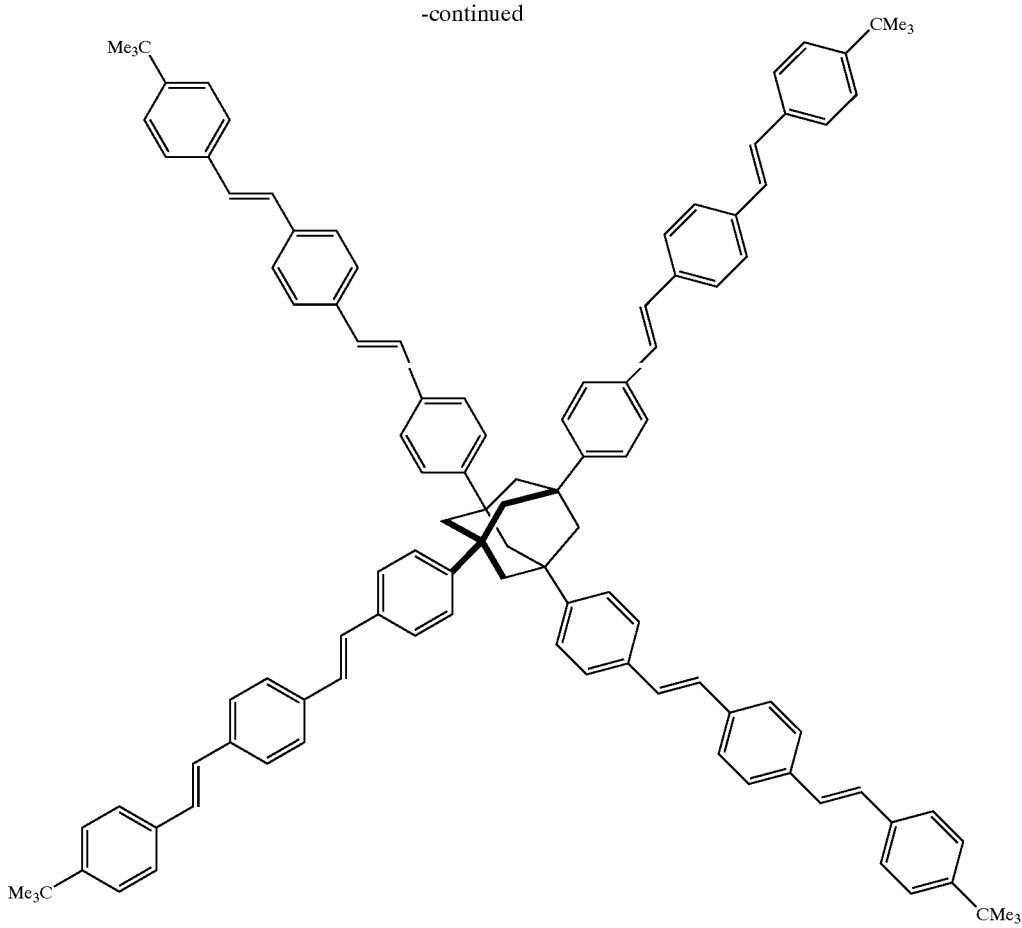

Ad(tBuSSB)4

Use of tetrakis(4-bromophenyl)silane (Si(C6H4Br)4) gives access to structural analogs containing a silicon atom at the tetrahedral junction. Thus, reaction of Si(C6H4Br)4 with excess styrene gives tetrastilbenylsilane (Si(STB)4) in 52% yield using Pd(OAc)2 under phase transfer conditions. Similarly, (Si(C6H4Br)4) and 4,4'-tert-butylvinylstilbene yields tetrakis(4-tert-butylstyrylstilbenyl)silane (Si(tBuSSB)4) in 40% yield.

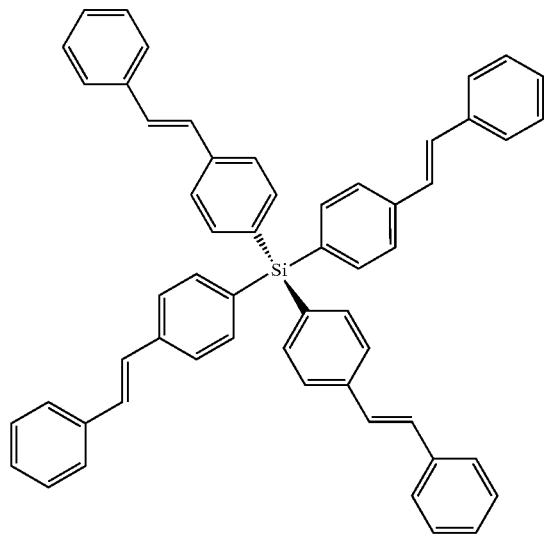

Si(STB)4

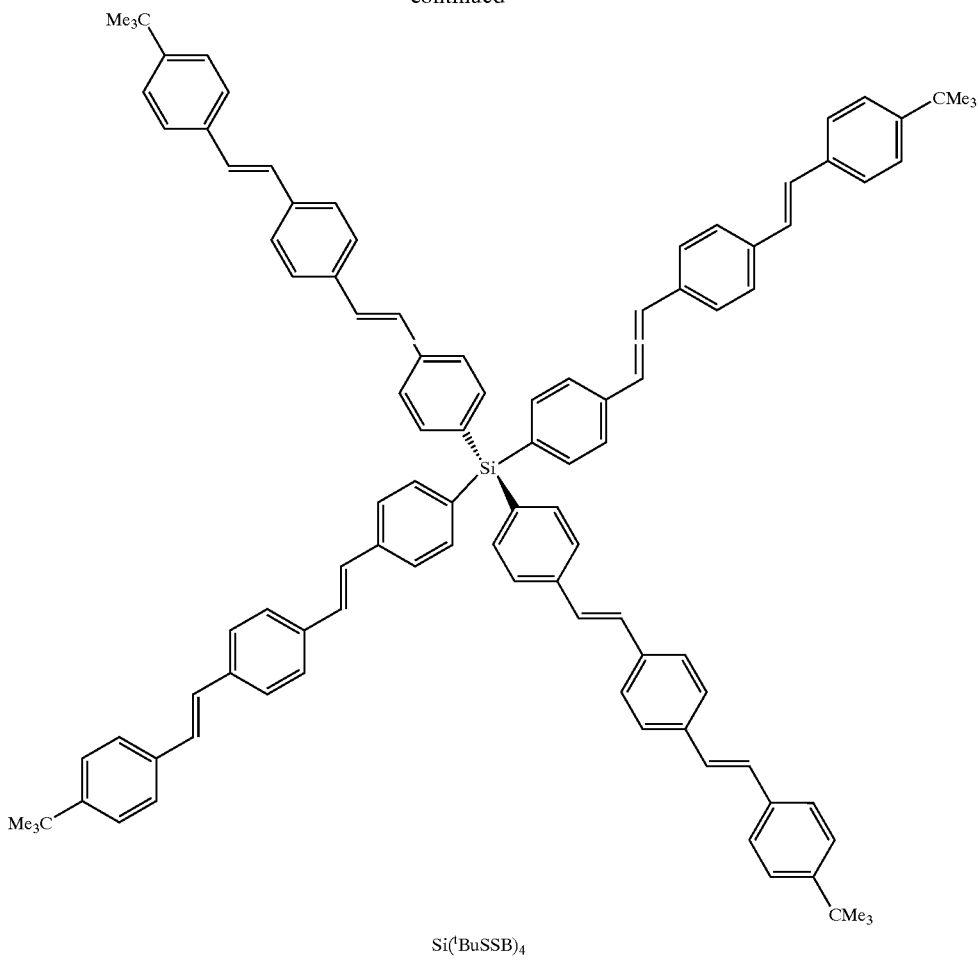

Si(tBuSSB)4

Morphology

Figure 3:
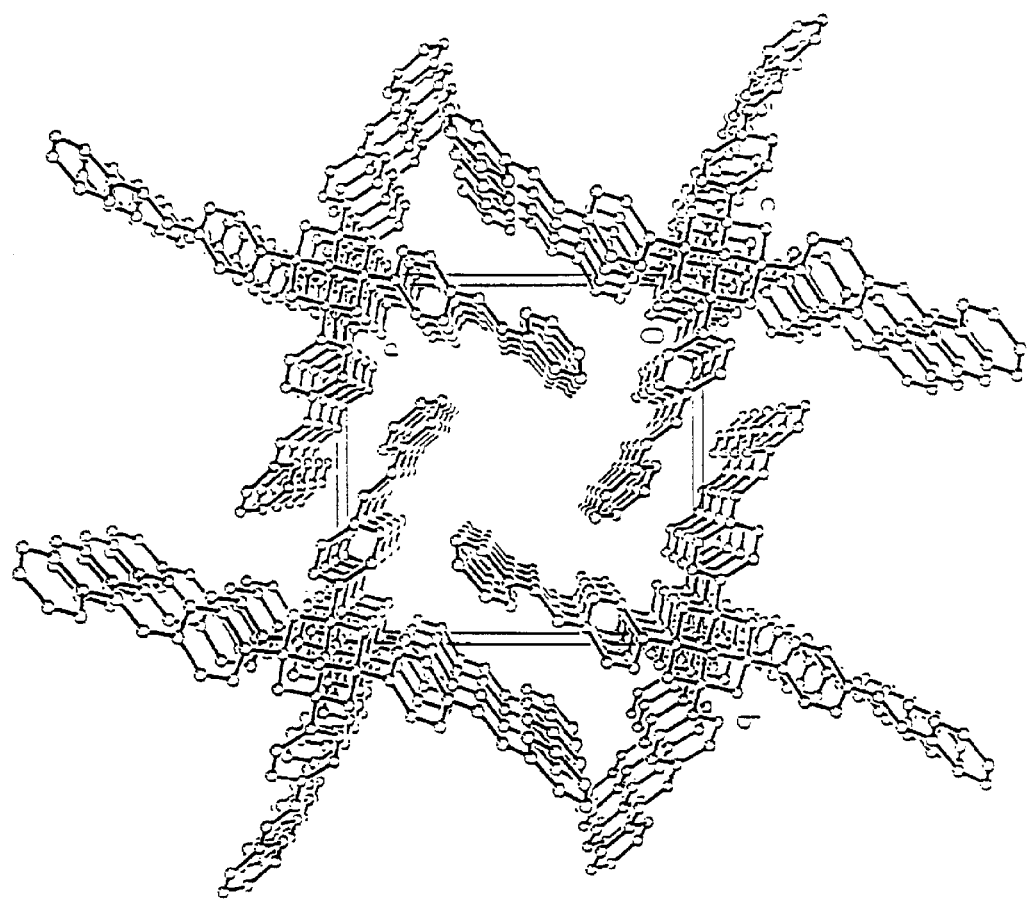
FIG. 3 shows the packing diagram of Ad(STB)$_4$ unit cell as viewed down the c axis.

We recently reported the single crystal X-ray study of C(STB)$_4$.[27] Two independent molecules were located on special positions (0, 0, 0 and 1/2, 1/2, 0) in the tetragonal unit cell P$\overline{4}$. A similar study was undertaken with Ad(STB)$_4$ using single crystals grown from methylene chloride and the results are shown in FIG. 3.

In the case of Ad(STB)$_4$, the solution to the structure was also done in the P$\overline{4}$ space group. There is an increase in the volume occupied per molecule from 1101.6(2)Å$^3$ to 1257.36 (7) Å$^3$ as a result of the larger adamantane core. The intramolecular metrical parameters and the separation between molecules observed for Ad(STB)$_4$ are normal. Thus, the two complexes have similar geometry and choose to pack in an isomorphous fashion. Both C(STB)$_4$ and Ad(STB)$_4$ show melting transitions by DSC at 274° C. and 306° C., respectively. Table 1 compares the thermal transitions determined for all compounds.

TABLE 1

Thermal analysis data by DSC.

| Compound | $T_g$, ° C. | $T_m$, ° C. |
|---|---|---|
| C(STB)$_4$ | | 274 |
| Si(STB)$_4$ | 81 | 179 |
| Ad(STB)$_4$ | | 306 |

TABLE 1-continued

Thermal analysis data by DSC.

| Compound | $T_g$, ° C. | $T_m$, ° C. |
|---|---|---|
| C(tBuSSB)$_4$ | 190 | |
| Si(tBuSSB)$_4$ | 191 | |
| Ad(tBuSSB)$_4$ | 165 | |
| C(DPVBi)$_4$ | 142 | |
| C(DPAB)$_4$ | 174 | |
| C(4R-tBu)$_4$ | 230 | |
| C(4R-2tBu)$_4$ | 181 | |
| 4R-2tBu | | 320 |
| 4R-(OC$_8$H$_{17}$)$_2$ | | 117 |
| T-4R—OC$_6$H$_{13}$ | 154 | |

Figure 4:
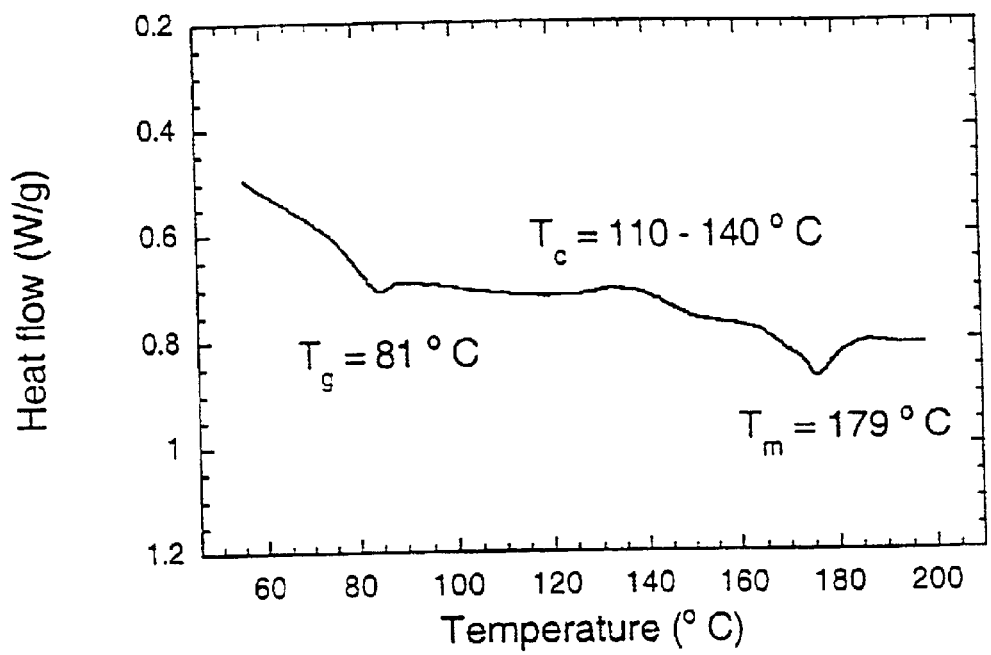
FIG. 4 shows DSC analysis of Si(STB)$_4$.

Compound Si(STB)$_4$ has interesting intermediate properties. FIG. 4 shows the DSC trace for thermally annealed Si(STB)$_4$. There is clear evidence of a glass transition at approximately 81° C. As the sample continues to be heated, a broad crystallization exotherm occurs in the 110–140° C. range. Finally melting occurs at approximately 179° C. Note that melting occurs at considerably lower temperatures than for C(STB)$_4$ or Ad(STB)$_4$ (Table 1). Similar melting point depressions for silicon-centered materials have been observed before. For example, the melting points of tetraphenylmethane and tetraphenylsilane are 285–286° C. and 224° C., respectively.

The larger compounds, such as E($^t$BuSSB)$_4$, C(DPVBi)$_4$, and C(DPAB)$_4$, readily form amorphous glasses with elevated glass transition temperatures (T$_g$=142–190° C.) in the absence of solvent.

Thermally annealed compounds with $^t$BuSSB substituents give kinetically stable amorphous phases (Table 1). These compounds are initially obtained as microcrystalline powders when precipitated from solution following synthesis and purification. Accordingly pristine samples typically show a weak and broad melting endotherm on the first heating cycle of a DSC experiment. Once residual solvent molecules are removed only amorphous phases are observed Spin casting films directly from chloroform solution results in transparent homogeneous films.

For C($^t$BuSSB)$_4$, we previously reported a glass transition at 175° C. More recent syntheses of this compound have yielded materials that gave an even higher glass transition at 190° C. While NMR data and elemental analysis obtained for different batches seem indistinguishable, GPC analysis indicates that the samples with T$_g$=175° C. contain a slightly higher fractions of cis-vinylic groups (15% compared to batches with T$_g$=190° C. that have a cis-fraction of only about 5%). It is likely that greater disorder expected in samples with a larger population of randomly distributed cis-linkages results in a reduction of T$_g$. The isomeric purity of the arms therefore is an important parameter for optimizing thermal stability. Compounds Ad($^t$BuSSB)$_4$ and Si($^t$BuSSB)$_4$ behave similarly with T$_g$s measured at 161° C. and 191° C. respectively.

Figure 5:
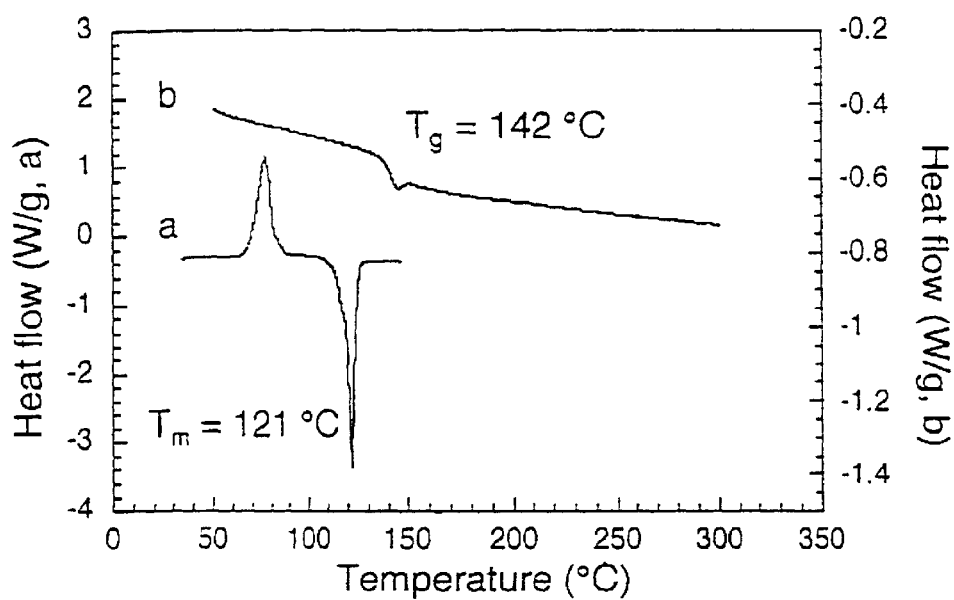
FIG. 5 shows DSC analysis of (a) 4-(2,2-Diphenylvinyl)-1,1'-biphenyl and (b) C(DPVBi)$_4$.

DSC analysis of C(DPVBi)$_4$ gives similar results to those obtained for the $^t$BuSSB tetramers. The first heating cycle reveals a broad endothermic transition centered at ca. 270° C. No transitions were observed upon cooling. Further heating cycles reveal only a step transition at 142° C., assigned to the glass transition of the amorphous sample (FIG. 5b). In comparison, 4-(2,2-diphenylvinyl)-1,1'-biphenyl (DVB) shows at melting endotherm on the first heating cycle at 121° C. (FIG. 5a). Upon cooling this sample at 10° C./min no crystallization transition was observed. Instead, in the next heating cycle the compound spontaneously crystallizes at 78° C., then T$_m$ is again observed at 121° C. This pattern is continuously observed in further heating/cooling cycles.

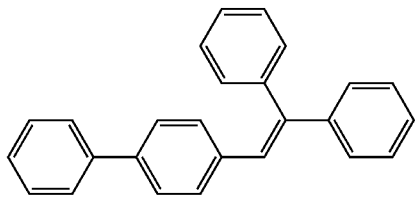

DVB

A slightly higher glass transition temperature was observed C(DPAB)$_4$ at 174° C. The elevated T$_g$ compared to C(DPVBi)$_4$, is consistent with stronger intermolecular interactions as the result of the more polar cyano functionality.

Studies on the larger molecules C(4R—$^t$Bu)$_4$, C(4R—2$^t$Bu)$_4$ and T—4R—OC$_8$H$_{17}$, confirm the observed trends. None shows a melting transition by DSC or evidence of crystalline regions by powder diffraction experiments. The component arms 4R-2$^t$Bu and 4R—(OC$_8$H$_{17}$)$_2$, are crystalline (Table 1) and lead to opaque films. Therefore, the tetrahedral strategy as means to design organic glasses extends to more conjugated fragments. In fact, comparison of C($^t$BuSSB)$_4$ (T$_g$=165° C.) against C(4R—$^t$Bu)$_4$ (T$_g$=230° C.) shows that considerably more stable films result when the chain length is extended by a single phenylenevinylene unit. No thermal transitions were observed for T—4ROC$_8$H$_{17}$, even when cooled to −30° C.

No evidence of crystallinity in samples of T—4R—OC$_6$H$_{13}$ nor T—4R—OC$_8$H$_{17}$ could be detected by powder X-ray diffraction data. Differential scanning calorimetry (DSC) measurements show that the glass transition temperature (T$_g$) of T—4R—OC$_6$H$_{13}$ occurs at 154° C. In the case of T—4R—OC$_8$H$_{17}$ a weak melting transition is observed at 179° C. The enthalpy of this transition (33.3 kJ/mole) suggests that this transition involves short range ordering of the octyloxy groups in T—4R—OC$_8$H$_{17}$, rather than long range order of the molecules themselves.

Optical Properties

Solution phase optical spectroscopic data of E($^t$BuSSB)$_4$ (E=C, adamantane, and Si) are characteristic of the parent distyrylbenzene chromophore. Films, however, show broad and significantly red-shifted emission spectra. In contrast, C(DPVBi)$_4$ gives absorption and emission spectra which are nearly identical between dilute solution phase samples and neat solid films. The emission of C(DPAB)$_4$ is broad and structureless, reminiscent of exciplex or excimer emission.

Films of the tetramers with longer arms (C(4R—$^t$BU)$_4$, C(4R—2$^t$Bu)$_4$, and T—4R—OC$_8$H$_{17}$ show emission properties which are dependent on sample history (Table 2). Annealing the sample at elevated temperature leads to red-shifted emission as a result of better interdigitation between the optically active fragments. Their behaviour is largely similar and only that of T—4R—OC$_8$H$_{17}$ will be discussed in detail as a representative example.

TABLE 2

Absorption and fluorescence emission data.

| Compound | $\lambda_{max}^{abs}$, nm$^a$ | $\lambda_{max}^{soln}$, nm$^b$ | $\lambda_{max}^{film}$, nm$^c$ | $\lambda_{max}^{annealed}$, nm$^d$ |
|---|---|---|---|---|
| C(4R-$^t$Bu)$_4$ | 389 | 432 | 472 | 511 |
| C(4R-2$^t$Bu)$_4$ | 386 | 431 | 479 | 515 |
| 4R-2$^t$Bu | 385 | 426 | 483 | 509 |
| T-4R-OC$_8$H$_{17}$ | 412 | 470 | 482 | 544 |
| 4R-(OC$_8$H$_{17}$)$_2$ | 407 | 466 | 482 | 510 |
| T-4R—OC$_6$H$_{13}$ | 392 | 431 | 479 | 515 |

$^a$Absorption maximum in CHCl$_3$.
$^b$Emission maximum in CHCl$_3$.
$^c$Emission maximum of thin film.
$^d$Emission maximum of thermally annealed thin film.

Figure 6:
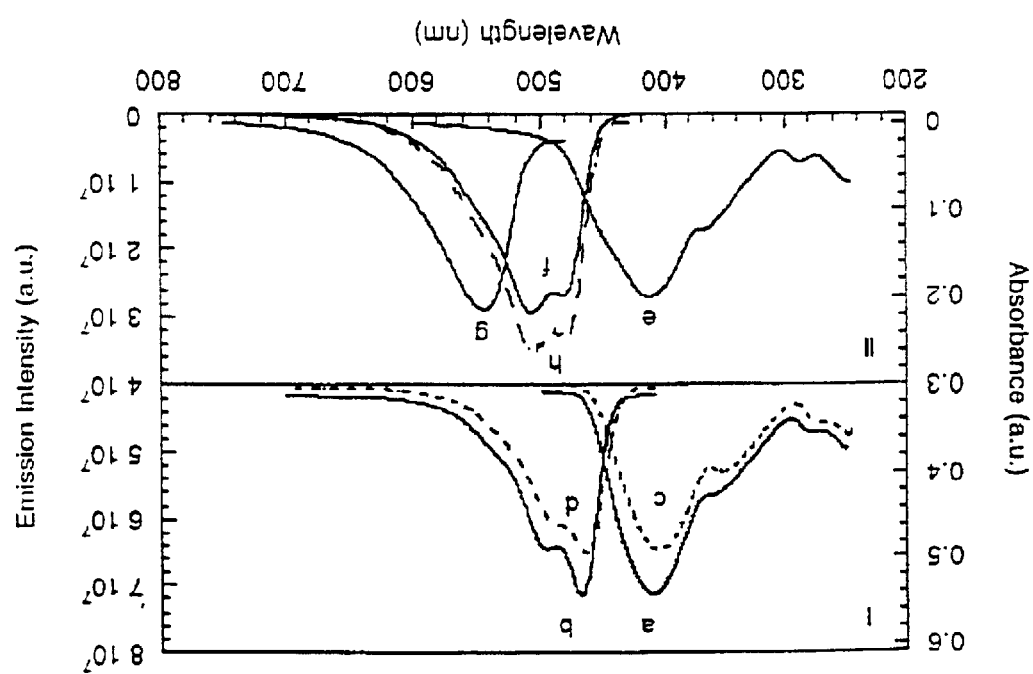
FIG. 6 Panel I shows: (a) absorption spectrum of T—4R—OC$_8$H$_{17}$ in CHCl$_3$; (b) fluorescence spectrum of T—4R—OC$_8$H$_{17}$ in CHCl$_3$; (c) absorption spectrum of 4R—(OC$_8$H$_{17}$)$_2$ in CHCl$_3$; (d) fluorescence spectrum of 4R—(OC$_8$H$_{17}$)$_2$ in CHCl$_3$. Panel II shows: (e) absorption spectrum of T—4R—OC$_8$H$_{17}$ (thin film); (f) fluorescence spectrum of T—4R—OC$_8$H$_{17}$ (thin film); (g) fluorescence spectrum of T—4R—OC$_8$H$_{17}$ (thermally annealed film); (h) fluorescence spectrum of T—4R—OC$_8$H$_{17}$ (thin film obtained after dissolving a thermally annealed sample)

As shown in FIG. 6, panel I, the fluorescence (FIG. 6a) and absorption spectra of T—4R—OC$_8$H$_{17}$ (FIG. 6b) in solution are similar to those of the parent chromophore 4R—(OC$_8$H$_{17}$)$_2$ (FIGS. 6c and 6d). Films have a broader absorption band (FIG. 6e) and their emission is red-shifted, relative to samples in solution (FIG. 6f). Heating films of T—4R—OC$_8$H$_{17}$ to 190° C. for 5 minutes under a nitrogen atmosphere leads to a red shift in emission (FIG. 6g). No changes occur in the absorption spectrum. Redissolving the annealed sample and recasting the film results in an emission spectrum identical to that of the original film (FIG. 6h). Therefore the process is reversible and is not likely to be due to impurities caused by thermal degradation. Our current thinking is that the "annealing" steps allows for the molecules to optimize interpenetration between chromophores and leads to environments suitable for excimer formation.

For T—4R—OC$_8$H$_{17}$ the absorption $\lambda_{max}$=413 nm (onset at 472 nm, 2.62 eV) and the photoluminescence maximum in chloroform occurs at 471 nm. After "annealing" the films at 200° C., a shift in emission to 545 nm is observed.

Figure 7:
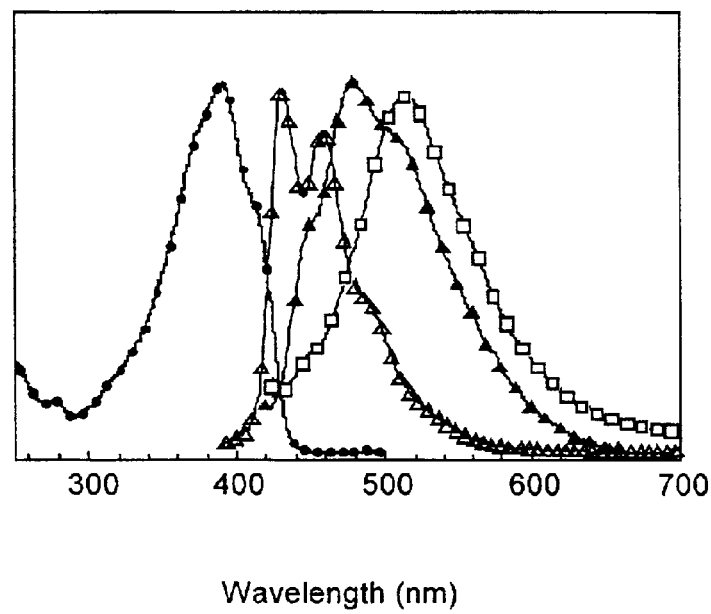
FIG. 7 shows: the absorption (●) spectrum, photoluminescence (Δ) spectrum in chloroform, neat film (▲) spectrum, and thermally annealed neat film (□) spectrum of tetrakis(4-(4'-(3",5"-dihexyloxystyryl)styryl)stilbenyl)methane.

FIG. 7 shows the optical data for T—4R—OC$_6$H$_{13}$. The absorption of T—4R—OC$_6$H$_{13}$ films has a maximum at $\lambda_{max}$=392 nm with an onset of at 440 nm, corresponding to a HOMO-LUMO gap of 2.82 eV. The emission from a chloroform solution has a maximum at 431 nm and a FWHM of c.a. 2700 cm$^{-1}$. The photoluminescence from a neat film on glass is red-shifted, with a maximum at 479 nm (FWHM of c.a. 4200 cm$^{-1}$). A further red shift to 515 nm (FWHM is ca. 3500 cm$^{-1}$) occurs upon annealing the samples by heating to 175° C., and then allowing them to cool to room temperature.

Figure 8:
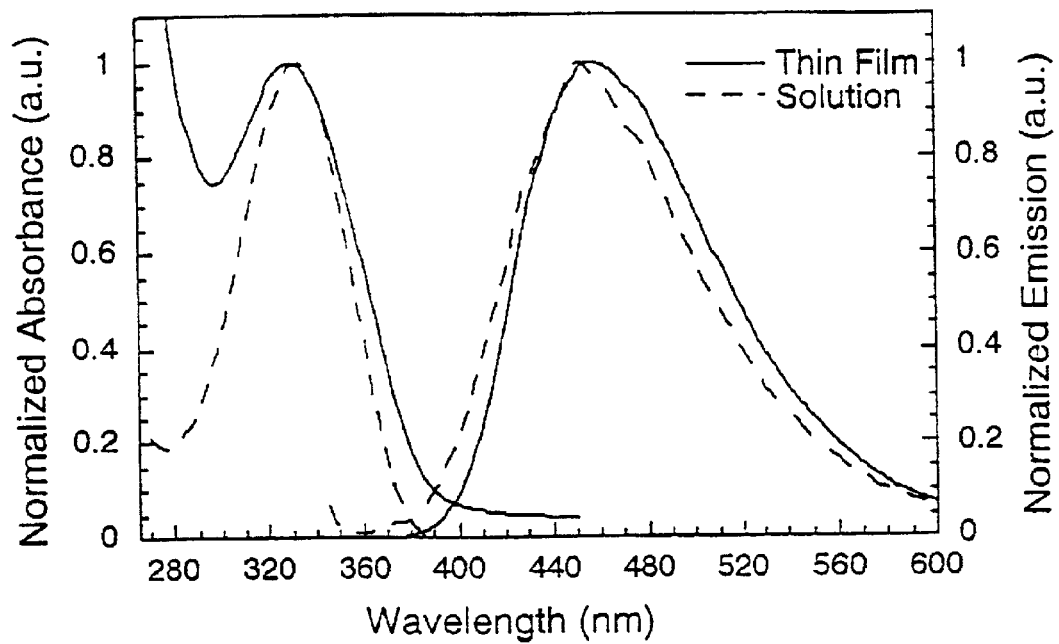
FIG. 8 shows absorption and emission spectra for C(DPVBi)$_4$ measured as dilute solutions or neat films on glass.

The absorption and fluorescence spectra of C(DPVBi)$_4$ is shown in FIG. 8 for both a sample in dilute solution and a neat film. Little distinction can be made in the optical spectra between the two different samples. However, while the fluorescence in solution is barely detectable by eye, the solid film glows with a brilliant blue fluorescence when excited with a hand held UV lamp. As is the case with DPVBi, the tetramer shows a large stokes shift and an unstructured absorption and fluorescence curve. In fact the spectra of DPVBi and C(DPVBi)$_4$ are virtually superimposable. We suspect that the rings on the periphery of the C(DPVBi)$_4$ molecule seal effectively the chromophores from interdigitation and prevent interchromophore contacts that lead to excimer formation.

Figure 9:
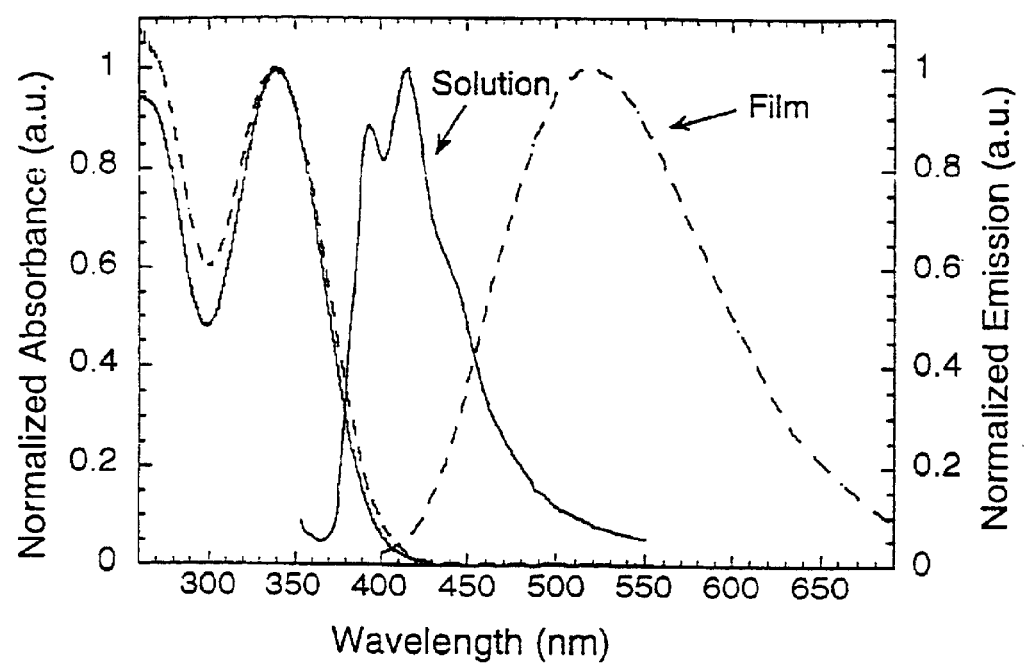
FIG. 9 shows absorption and emission spectra for C(DPAB)$_4$ measured as dilute solutions and neat films on glass.

Very little difference can be discerned in the absorption spectra of solution phase samples or neat films of C(DPAB)$_4$ (FIG. 9). The corresponding fluorescence data are remarkably different. Emission in solution is centered at ca. 416 nm and shows distinct vibronic coupling. The neat film gives a broad red-shifted fluorescence centered at ca. 519 nm that is reminiscent of exciplex emission. These data suggest interactions between the carbonitrile functionality and the chromophore in the excited state.

Fabrication of Electroluminescent Devices Using Soluble Tetrahedral Tetramers.

A layer of an EL device containing the tetrahedral compound of the present invention can be fabricated by spin-casting. To prepare solutions of soluble tetrahedral tetramers, the material is stirred in the selected solvent at room temperature for several hours. After a clear solution is formed, it is filtered through a 0.45 micron filter. Pinhole-free, uniform films can be obtained by spin-casting the solution at room temperature. Preferably, the cast speed is in the range of 400 rpm to 5000 rpm. High quality films with thickness of 300–5000 Å can be obtained by varying the spin speed and the concentration of the solution. Films with thickness from 0.03–20 micrometers can also be prepared in large areas by dip casting and drop casting.

Thin films of the tetrahedral tetramers are transparent to visible light and have an absorption edge which can be tuned according to the molecular structure and the number of repeat units in the oligomeric fragments. Typical absorption edges are in the range 300 to 700 nm, depending on the molecular structure. The color of the emission can also be controlled by changing the molecular structure and number of repeat units in the optoelectronic arms.

The soluble tetrahedral tetramers materials disclosed in this invention can be used to fabricate thin film devices in the anode-semiconductor-cathode sandwich configuration well-known in the art[41]. When the anode and cathode have different work functions, these thin film devices function as diodes which show rectification characteristics which can be used for electrical switching applications, and they can function as light emitting diodes, as photo-detecting diodes and as photovoltaic cells[42].

Metallic materials with work-function higher than 4.5 eV such as Au, Ag, Ni, Cu, Se, PANI can be used as the anode electrode in these devices. Preferably, Indium-tin-oxide (ITO) coating on glass substrates is used as the transparent anode. Poly(ethylenedioxythiophene) (PEDOT) and polyaniline (PANI) are conductive polymers which are semi-transparent as thin films[43]. For some applications, bilayer electrodes comprising ITO/PEDOT or ITO/PANI are used as the transparent anode[44].

Metallic materials with relatively low work-function (lower than 4.5 eV) such as Ba, Li, Ce, Cs, Eu, Rb, and Sm are preferred as the cathode materials of the devices[45]. For light emission, preferably calcium or, more preferably, barium is used as the cathode electrode. The thickness of the polymer layer is less than 1000 nm and preferably less than 100 nm. Ultrathin metal oxide layers, such as BaO, can also be used for efficient electron injection.

The efficiency of light emitting devices (LEDs) fabricated using the soluble tetrahedral tetramers disclosed in this invention can be improved by including an electron and/or hole transport agent with the tetrahedral compound, either as a composition or as a separate charge transport layer. Examples of electron transport agents include 1-(4Bipenyl)-5-(4-tertbutyl-phenyl)-1,3,4-oxadioazole (PBD) and AlQ3. Examples of hole transport agents include polyvinylcarbazole (PVK), polyphenylvinylene (PPV) and Bis(3-methylphenyl)diphenylbenzidine (TPD).

Preferred versions of the device include at least two layers consisting of an electroluminescent layer, an electron transport layer, and/or a hole transport layer, where at least one of the layers contains the tetrahedral compound of the present invention. In a most preferred version of the device, a hole transport layer comprising an arylamine, such as polyvinylcarbazole (PVK), is inserted between anode layer and the layer containing the tetrahedral compound of the present invention.

Blends comprising tetrahedral tetramer as host and green or red emitting species as guest can be used as electroluminescent materials to generate light with longer wavelength emission. In this case, electrons and holes are injected into the $\pi^*$ and $\pi$ bands, respectively of the host PFO. Longer wavelength emission follows excitation transfer to the guest species[46].

As demonstrated in the Examples below, light emission with external quantum efficiency approaching 1% ph/el can be achieved with light-emitting diodes (LEDs) based on the soluble tetrahedral tetramers. These electroluminescent devices can be operated at low bias voltage. Light emission is typically observed above 3–4 volts and reaches ~100 cd/m$^2$ at ~4–6 V.

High EL efficiency can be achieved by improving hole injection into the tetrahedral tetramers layer using materials such as PVK (work function 5.5 eV) and PEDOT (work function 5.2 eV). A summary of device data is given in the Examples below (see Table 3).

Conclusion

In summary, we have shown that it is possible to minimize the tendency of conjugated organic fragments to crystallize by coordinating them around a tetrahedral junction site. The length of the monomeric unit needs to reach a minimum length to obtain a stable amorphous phase. For the relatively small stilbene arms, the materials crystallize readily. It is interesting in this respect that the methane and adamantane cores give isomorphous crystal lattices with an increase in cell dimensions commensurate with the core volume. Compound Si(STB)$_4$ is an intermediate case and displays thermal transitions corresponding to glassy and crystalline phases.

Kinetically stable amorphous morphologies are obtained with the distryrylbenzene arms. The series C($^t$BuSSB)$_4$, Ad($^t$BuSSB)$_4$ and Si($^t$BuSSB)$_4$ shows that the choice of tetrahedral core determines the glass transition temperature. Exactly how the chemical and dimensional qualities of the inner core influences $T_g$, even for a family of closely related set of compounds, remains unanswered at the present time. Nonetheless, the molecular qualities of the inner core are a useful parameter to optimize the stability of the resulting films for a specific application. As the conjugation length of the monomeric unit is further increased, only amorphous materials are obtained. The compounds C(4R—$^t$Bu)$_4$, C(4R-2$^t$Bu)$_4$ and T—4R—OC$_8$H$_{17}$ display the highest glass transition temperatures and have excellent film forming properties.

The thermal properties of C(DPVBi)$_4$ and C(DPAB)$_4$ illustrate nicely how the tetrahedral approach discourages crystallization without the need to substitute the basic chromophore skeleton with aliphatic sidegroups. It is noteworthy that each of these compounds is initially obtained as a crystalline material following conventional organic solvent crystallization procedures. In the case of C(DPVBi)$_4$, solvent molecules are incorporated in the crystal lattice. For example colorless crystals that have only been briefly exposed to vacuum analyze correctly for C$_{105}$H$_{76}$•1/3CHCl$_3$ (see experimental section for details). During the first heating cycle of the DSC analysis, solvent is removed and the long range order in the crystalline material is disrupted to give an amorphous solid. The melted material becomes trapped in a disordered state upon cooling because reversible molecular associations that are conducive to crystal growth are hindered in the absence of solvent.

Comparison of solution and solid state optical data indicates that multiple environments are present in the solid state. In particular, the broad emission from films of $^t$BuSSB containing tetramers strongly suggests formation of excimer sites. The reversible red-shift in emission observed for films of C(4R—$^t$Bu)$_4$, C(4R—2$^t$Bu)$_4$ and T—4R—OC$_8$H$_{17}$ upon heating is consistent with this idea. It is likely that the molecules are able to interdigitate better with the additional thermal energy and the enhanced mixing gives excimer forming sites. Because of energy migration, it is not possible to quantitate the fraction of chromophores that participate in excimer formation. In the case of the DPVBi fragment, the terminal phenyl rings enclose the outer surface of the tetrahedral molecule and prevent close contacts along the long axis of the chromophore. Each chromophore is thus insulated from its partners and behaves independently.

The synthetic methods described herein provide a suitable platform for accessing a wide range of chemical structures with properties appropriate for inclusion in optoelectronic devices. Addition of electron withdrawing or releasing substituents is easily envisioned for fine-tuning charge injection properties, charge migration and emission color.

EXAMPLES

General Experimental Details

All manipulations involving air-sensitive organometallic reagents were carried out as described previously.[47] $^1$H and $^{13}$C NMR spectra were recorded on a Bruker AMX-400 NMR spectrometer operating at 400.1 and 100.6 MHz, respectively. UV-vis absorption spectra were recorded on a Perkin-Elmer Lambda 19 spectrophotometer and photoluminescence spectra on a Spex Fluorolog 2 spectrometer in spectral grade chloroform. High resolution mass spectrometry was performed by the Nebraska Center for Mass Spectrometry at the University of Nebraska-Lincoln. Elemental analyses were performed by Desert Analytics. Reagents were obtained from Aldrich and used as received. Flash chromatographic separations were carried out using the Biotage Flash 40 system. Differential scanning calorimetry experiments were carried out using a TA Instruments model 2920 DSC.

4-(4'-Vinylstyryl)benzaldehyde.

Solid NaH (360 mg, 15 mmol) was added in small portions into a suspension of terephthaldehyde mono-(diethylacetal) (1.95 g, 9.09 mmol) and 4-vinylbenzyltriphenylphosphonium chloride (4.13 g, 10 mmol). The reaction mixture was stirred under nitrogen at room temperature for 24 hours. The reaction was quenched slowly with water, extracted with CHCl$_3$, washed with brine, dried over MgSO$_4$ and the solvent was evaporated under reduced pressure. The oily light yellow solid was dissolved in a mixture of 10 mL THF, 10 mL water and 5 mL acitic acid and stirred for 30 min at room temperature. The solvents was removed to dryness. The crude product was purified on a silica gel column (20–40 CH$_2$Cl$_2$/hexanes) to give a light yellow solid. Yield 2.0 g (94%). $^1$H NMR (CDCl$_3$): δ 7.87 (d, J=8.0 Hz, 2H), 7.67 (d, J=8.0 Hz, 2H), 7.52 (d, J=8.0 Hz, 2H), 7.43 (d, J=8.0 Hz, 2H), 7.26 (d, J=16.0 Hz, 1H), 7.14 (d, J=16.0 Hz, 1H), 6.73 (dd, J$_1$=17.6 Hz, J$_2$=11.2 Hz, 1H), 5.80 (d, J=11.2 Hz, 1H), 5.29 (d, J=11.2 Hz, 1H). $^{13}$C NMR (CDCl$_3$): δ 191.54, 143.31, 137.67, 136.19, 135.94, 131.66, 130.17, 127.08,127.02, 126.79, 126.58, 114.27.

1-(4'-tert-butylstyryl)-4-(4'-vinylstyryl)benzene.

Solid NaH (396 mg, 16.5 mmol) was added in small portions into a suspension of 4-(4'vinylstyryl)benzaldehyde (703 g, 3.0 mmol) and 4-tert-butylbenzyltriphenylphosphonium bromide (1.61 g, 3.3 mmol). The reaction mixture was stirred under nitrogen at room temperature for 24 hours. The reaction was quenched slowly with water, extracted with CHCl$_3$, washed with brine, and the solvent was evaporated under reduced pressure to dryness. To the residue, 100 mL of dry toluene was added and evaporated to dryness. The light yellow solid was triturated with ethanol, filtered to give light yellow solid (which is the all-trans isomer by NMR). The filtrate was concentrated and purified with silica gel chromatography (10–20% CHCl$_3$/hexanes) to give another portion of product (a mixture of cis and trans isomers). Yield: 1.1 g (>99%). $^1$H NMR (CDCl$_3$) of the all-trans isomer: δ 7.51 (s, 4H), 7.49, 7.47 (d, J=8.46 Hz, 4H), 7.41, 7.39 (d, J=8.45 Hz, 4H), 7.13, 7.07 (d, J=16.28 Hz, 2H), 7.11 (s, 2H), 6.72 (dd, J$_1$=10.85 Hz, J$_2$=17.55 Hz, 1H), 5.78 (d, J=17.55 Hz, 1H), 5.26 (d, J=10.85 Hz, 1H), 1.34 (s, 9H). The compound is too insoluble for $^{13}$C NMR spectroscopy.

Tetrakis(4-(4'-(4"-tert-butylstyryl)styryl)stilbenyl)methane (C(4R—$^t$Bu)$_4$).

A 50 mL round bottom flask was charged with a Teflon coated stir bar, tetrakis(4-iodophenyl)methane (154.5 mg, 0.1875 mmol), 1-(4'-tert-butylstyryl)-4-(4'-vinylstyryl) benzene (1.1 g, 3.0 mmol), Pd(OAc)$_2$ (8.4 mg, 10 mol %), K$_2$CO$_3$ (258 mg, 1.875 mmol), n-Bu$_4$NBr (249 mg, 0.75 mmol) and N,N-dimethylformamide (DMF) (25 mL). The mixture was degassed with 4 freeze-pump-thaw cycles and heated at 90° C. for 72 hours. The reaction was cooled to room temperature, diluted with CH$_2$Cl$_2$, washed with brine, dried over MgSO$_4$ and the solvent was removed under reduced pressure. The low solubility of the product makes it difficult to extract the product from the reaction. A small amount of crude material was purified on a silica gel column (30% CHCl$_3$/hexanes) to give a yellow solid which is a mixture of cis-trans isomers. The isomers were dissolved in 80 mL benzene and degassed with 4 freeze-pump-thaw cycles. The solution was irradiated with Blak-Ray long UV lamp for 30 minutes and the solvent was removed under reduced pressure. The isomerized product was triturated with chloroform and filtered to give a yellow solid (yield 39 mg). $^1$H NMR (CDCl$_3$): δ 7.06–7.55 (aromatic and vinylic —CH=, complex, 21 H), 1.38 (s, 18H). The compound was too insoluble for $^{13}$C NMR spectroscopy. Calcd for C$_{137}$H$_{124}$: C, 92.94; H, 7.06. Found: C, 92.73; H, 7.21.

1-(3'5'-di-tert-butylstyryl)-4-(4'-vinylstyryl)benzene.

Solid NaH (396 mg, 16.5 mmol) was added in small portions into a suspension of 4-(4'-vinylstyryl)benzaldehyde (703 g, 3.0 mmol) and 3,5-di-tert-butylbenzyltriphenylphosphonium bromide (2.09 g, 3.3 mmol). The reaction mixture was stirred under nitrogen at room temperature for 22 hours. The reaction was quenched slowly with water, extracted with CHCl$_3$, washed with brine, dried over MgSO$_4$ and the solvent was evaporated under reduced pressure. The crude product was purified on a silica gel column (20% CHCl$_3$/hexanes) to give a greasy yellow solid which is a mixture of cis-trans isomers. Yield 1.30 g (>99%). $^1$H NMR (CDCl$_3$): δ 7.00–7.56 (complex, 14H), 6.50–6.77 (complex, 2H), 5.71–5.81 (complex, 1H), 5.22–5.30 (complex, 1H), 1.45, 1.39, 1.38, 1.34, 1.26 (s, 18H).

Tetrakis(4-(4'-(3", 5"-di-tert-butylstyryl)styryl)stilbenyl) methane (C(4R—2'Bu)$_4$).

A 100 mL round bottom flask was charged with a magnetic stir bar, tetrakis(4-iodophenyl)methane (206 mg, 0.25 mmol), 1-(3'5'-di-tert-butylstyryl)-4-(4'-vinylstyryl)benzene (1.3 g, 3.0 mmol), Pd(OAc)$_2$ (12 mg, 0.0535 mmol), K$_2$CO$_3$ (345 mg, 2.5 mmol), n-Bu$_4$NBr (332 mg, 1.0 mmol) and DMF (30 mL). The mixture was degassed with 4 freeze-pump-thaw cycles and heated at 90° C. for 63 hours. The reaction was cooled to room temperature, diluted with CH$_2$Cl$_2$, washed with brine, dried over MgSO$_4$ and the solvent was removed under reduced pressure. The crude product was purified on a silica gel column (20–40% CH$_2$Cl$_2$/hexanes) to give a yellow greasy solid which is a mixture of cis-trans isomers. The isomers were dissolved in 100 mL benzene and degassed with 4 freeze-pump-thaw cycles. The solution was irradiated with Blak-Ray long UV lamp for 30 minutes and the solvent was removed under reduced pressure. The isomerized product was repurified on a silica gel column (30% CH$_2$Cl$_2$/hexanes) to give a yellow solid (yield 74%). $^1$H NMR (CDCl$_3$): δ 7.06–7.55 (overlapping aromatic and vinylic signals, 21H), 1.38 (s, 18H). $^{13}$C NMR (CDCl$_3$): δ 151.27, 146.28, 136.94, 136.70, 136.64, 135.28, 131.51, 129.94, 129.50, 128.43, 128.20, 127.76, 127.06, 127.00, 126.51, 126.04, 123.59, 122.39, 121.10, 94.60, 31.55. Calcd for C$_{153}$H$_{156}$: C, 92.12; H, 7.88. Found: C, 91.87; H, 8.11.

4-(4'-(3", 5"-Di-tert-butylstyryl)styryl)stilbene (4R—2'Bu).

A 50 mL round bottom flask was charged with a Teflon coated stir bar, 4-iodophenylmethane (408 mg, 2.0 mmol), 1-(3'5'-di-tert-butylstyryl)-4-(4'-vinylstyryl)benzene (0.84 g, 2.0 mmol), Pd(OAc)$_2$ (22.45 mg, 0.1 mmol), K$_2$CO$_3$ (690 mg, 5.0 mmol), n-Bu$_4$NBr (665 mg, 2.0 mmol) and DMF (16 mL). The mixture was degassed with 4 freeze-pump-thaw cycles and heated at 90° C. for 48 hours. The reaction was cooled to room temperature, diluted with CH$_2$Cl$_2$, washed with brine, dried over MgSO$_4$ and the solvent was removed under reduced pressure. The crude product was purified on a silica gel column (20% CH$_2$Cl$_2$/hexanes) to give a yellow greasy solid which contains cis-trans isomers. The isomers were dissolved in 150 mL benzene and degassed with 4 freeze-pump-thaw cycles. The solution was irradiated with Blak-Ray long UV lamp for 60 minutes and the solvent was removed under reduced pressure. The isomerized product was repurified on a silica gel column (20% CH$_2$Cl$_2$/hexanes) to give a yellow solid (yield 71%). $^1$H NMR (CDCl$_3$): δ 7.51–7.54 (overlapping signals, 9H), 7.35–7.39 (overlapping signals, 5H), 7.28 (t, J=7.50 Hz, 1H), 7.19 (d, J=16.3 Hz, 1H), 7.13 (complex, 4H), 7.10 (d, J=16.3 Hz, 1H), 1.37 (s, 18H). $^{13}$C NMR (CDCl$_3$): δ 151.28, 137.54, 136.66, 129.96, 128.93, 128.78, 128.49, 128.20, 127.76, 127.09, 127.04, 127.01, 126.73, 121.09, 31.69. Exact Mass (FAB, NBA) for M$^+$ (C$_{38}$H$_{40}$): calculated 496.3143; found 496.3189.

Dioctoxy-1-styryl-4-(4'-vinylstyryl)benzene.

Solid NaH (300 mg, 12.4 mmol) was added in small portions into a suspension of 2,5-dioctoxy-4-(4'-vinylstyryl) benzaldehyde (1.27 g, 2.59 mmol) and benzyltriphenylphosphonium bromide (1.35 g, 3.11 mmol). The reaction mixture was stirred under nitrogen at room temperature for 24 hours. The reaction was quenched slowly with water, extracted with CH$_2$Cl$_2$, washed with brine, dried over MgSO$_4$ and the solvent was evaporated under reduced pressure. The crude product was purified on a silica gel column (25–40% CHCl$_3$/hexanes) to give a greasy yellow solid which is a mixture of cis and trans isomers. Yield 1.2 g (82%). $^1$H NMR (CDCl$_3$): δ 7.51 (d, J=9.26 Hz, 2H), 7.47 (d, J=9.25 Hz, 1H), 7.42 (s, 2H), 7.29 (d, J=7.36 Hz, 2H), 7.25 (dd, J$_1$=6.38 Hz, J$_2$=7.36 Hz, 2H), 7.18 (t, J=7.34 Hz, 1H), 7.14 (s, 1H), 6.76 (d, J=11.97 Hz, 1H), 6.72 (dd, J$_1$=17.72 Hz, J$_2$=10.85 Hz, 1H), 6.34 (d, J=12.00 Hz, 1H), 5.78 (d, J=17.72 Hz, 1H), 5.25 (d, J=10.85 Hz, 1H), 4.02 (t, J=6.54 Hz, 2H), 3.55 (t, J=6.87 Hz, 2H), 1.78 (m, 4H), 1.64 (m, 4 H), 1.23–1.42 (m, 16H), 0.90 (m, 6H). $^{13}$C NMR (CDCl$_3$): δ 151.34, 150.35, 137.89, 137.79, 136.81, 136.72, 130.24, 129.12, 128.49, 128.36, 127.14, 126.84, 126.73, 126.70, 125.62, 123.74, 114.81, 113.71, 110.37, 69.56, 69.16, 32.06, 29.61, 29.51, 26.33, 22.90, 14.35. FABMS: m/z 564 (M$^+$).

Tetrakis((4-(2'5'-dioctoxy-4'styryl)styryl)stilbenyl)methane (T—4R—OC$_8$H$_{17}$).

A 50 mL round bottom flask was charged with a Teflon coated stir bar, tetrakis(4-iodophenyl)methane (145.6 mg, 0.177 mmol), 2,5-dioctoxy-1-styryl-4-(4'-vinylstyryl) benzene (1.2 g, 2.12 mmol), Pd(OAc)$_2$ (8 mg, 0.035 mmol), K$_2$CO$_3$ (244 mg, 1.77 mmol), n-Bu$_4$NBr (235 mg, 0.708 mmol) and DMF (20 mL). The mixture was degassed with 3 freeze-pump-thaw cycles and heated at 90° C. for 3 days. The crude product mixture was then diluted with methanol and filtered to give a yellow greasy solid. The crude was purified on a silica gel column (30% CH$_2$Cl$_2$/hexanes) to give a yellow greasy solid which is a mixture of five cis-trans isomers (by HPLC). The isomers were dissolved in 100 mL benzene and degassed with 3 freeze-pump-thaw cycles. The solution was irradiated with Blak-Ray long UV lamp for 60 minutes and concentrated under reduced pressure. The residue was diluted with methanol and filtered off to give a yellow solid (yield: 330 mg, 72%). $^1$H NMR (CDCl$_3$): δ 7.49–7.56 (m, 28H), 7.47 (d, J=6.70 Hz, 8H), 7.45 (s, 4H), 7.36 (dd, J=7.50 Hz, J$_2$=7.66 Hz, 8H), 7.29 (d, J=8.46 Hz, 8H), 7.25 (t, J=7.66 Hz, 4H), 7.16 (s, 4 H), 7.13 (s, 8H), 7.12 (s, 12H), 4.06 (t, J=6.38 Hz, 16H), 1.88 (m, 16H), 1.19–1.43 (m, 80H), 0.90 (m, 24H). $^{13}$C NMR (CDCl$_3$): δ 151.34, 137.88, 137.65, 136.72, 131.52, 130.21, 129.14, 128.86, 128.65, 128.37, 128.11, 127.15, 127.03, 126.74, 126.03, 125.64, 123.71, 114.84, 69.80, 69.20, 32.05, 29.74, 29.50, 26.52, 22.91, 14.35. Calcd for C$_{185}$H$_{250}$: C, 86.40; H, 8.62. Found: C, 86.09; H, 8.92.

Tetrakis(4-(4'-(3", 5"-dihexyloxystyryl)styryl)stilbenyl) methane.

A 100 mL round bottom flask was charged with a Teflon coated stir bar, tetrakis(4-iodophenyl)methane (186 mg, 0.225 mmol), 1-Vinyl-4-(3', 5'-dihexyloxy)styrylstilbene (1.37 g, 2.7 mmol), palladium acetate (10 mg, 0.0445 mmol), K$_2$CO$_3$ (310 mg, 2.25 mmol), NBu$_4$Br (299 mg, 0.9 mmol) and anhydrous DMF (30 mL), The mixture was degassed with 4 freeze-pump-thaw cycles and heated at 90° C. for 63 hours. The reaction was cooled to room temperature, diluted with dichloromethane, washed with brine, dried over magnesium sulfate and the solvent was removed under reduced pressure. The crude product was purified on a silica gel column (30–50% dichloromethane/ hexanes) to give a yellow greasy solid which contains cis-trans isomers. The isomers were dissolved in 100 mL benzene and degassed with 4 freeze-pump-thaw cycles. The solution was irradiated with a Black-Ray long UV lamp for 30 minutes and the solvent was removed under reduced pressure. The isomerized product was repurified on a silica gel column (30% dichloromethane/hexanes) to give a yellow solid (yield 80%). $^1$H NMR (400 MHz, CDCl$_3$): δ 7.36–7.50 (complex, 8H), 7.25 (d, J=8.0 Hz, 2H), 7.16 (d, J=8.0 Hz, 2 H), 7.07, 7.35 (d, J=16.0 Hz, 2H), 7.05 (s, 2H), 6.65 (d, J=2.08 Hz, 2H), 6.40 (t, J=2.08 Hz, 1H), 3.97 (t, J=6.22 Hz, 4H), 1.79 (m, 4H), 1.47 (m, 4H), 1.35 (m, 8H), 0.92 (m, 6H). $^{13}$C NMR (100 MHz, CDCl$_3$) δ 160.68, 146.25, 139.37, 136.80, 135.21, 131.56, 128.88, 128.70, 128.52, 128.30, 127.10, 105.29, 101.15, 68.27, 31.83, 29.50, 25.97, 22.84, 14.28. Anal: calcd (C$_{169}$H$_{188}$O$_8$): C, 86.47; H, 8.07. Found: C, 86.55; H, 8.01.

Tetrakis(3,5-dimethoxystyrylstilbenyl)methane.

A mixture of the tetrakis(4-iodophenyl)methane (0.3 mmol, 248 mg), 1-vinyl4-(3', 5'-dimethoxystyryl)benzene (1.8 mmol, 480 mg), Pd(OAc)$_2$ (4.7 mg, 7 mol %), K$_2$CO$_3$ (1.2 mmol, 166 mg), n-Bu$_4$NBr (1.2 mmol, 388 g) in 15 mL DMA was purged with nitrogen and heated at 105° C. with stirring under nitrogen for 72 hours. The reaction mixture was allowed to cool down to room temperature. The product was precipitated with MeOH and centrifuged. The solid residue was taken up into benzene and centrifuged. The clear solution was collected and solvent evaporated. The crude product was purified with silica gel chromatography (CHCl$_3$: hexanes=3:1) to give yellow solid (25% yield). $^1$H-NMR (400 MHz, CDCl$_3$): δ ppm 7.50 (s, 16H), 7.44 (d, J=8.5 Hz, 8H), 7.28 (d, J=8.5 Hz, 8H), 7.11 (dd, J=16.4 Hz, 8H), 7.07 (dd, J=16.4 Hz, 8H), 6.68 (d, J=2.1 Hz, 8H), 6.41 (t, J=2.1 Hz, 4H), 3.84 (s, 24H). $^{13}$C-NMR (100 MHz, CDCl$_3$): δ ppm 160.9, 146.0, 139.2, 136.7, 136.4, 135.0, 131.2, 128.7, 128.4, 128.2, 128.0, 126.8, 126.7, 125.7, 104.4, 99.9, 55.3, 29.6.

Tetrakis((4-(2', 5'-dioctyloxy-4'-(4"-(2'"5'"-dioctyloxy-4'"styryl)styryl)styryl)styryl)stilbenyl)methane.

A 100 mL round bottom flask was charged with a Teflon coated stir bar, tetrakis(4-iodophenyl)methane (285 mg, 0.346 mmol), 1-(2', 5'-dioctyloxy-4'-(4"-vinyl)styryl)styryl-4-(2', 5'-dioctyloxy-4'-styryl)styrylbenzene (3.0 g, 2.77 mmol), Pd(OAc)$_2$ (15 mg, 0.0668 mmol), K$_2$CO$_3$ (480 mg, 3.5 mmol), n-Bu$_4$NBr (461 mg, 1.39 mmol) and anhydrous DMF (30 mL), The mixture was degassed with 4 freeze-pump-thaw cycles and heated at 80° C. for 2 days. The reaction was cooled to room temperature, diluted with CH$_2$Cl$_2$, washed with brine, dried over MgSO$_4$ and the solvent was removed under reduced pressure. The crude was purified on a silica gel column (30–60% CHCl$_3$/hexanes) to give a yellow greasy solid which contains cis-trans isomers. The isomers were dissolved in 100 mL benzene and degassed with 4 freeze-pump-thaw cycles. The solution was irradiated with long UV light for 60 minutes and benzene was removed under reduced pressure. The isomerized product was repurified on a silica gel column (30% CHCl$_3$/ hexanes) to give 1.1 g (73%) yellow solid. $^1$H NMR (400 MHz, CDCl$_3$): δ 7.10–7.56 (aromatic and vinylic —CH═, complex, 31H), 4.07 (t, 6.54H), 1.89 (m, 8H), 1.55 (m, 8H), 1.24–1.44 (m, 32H), 0.90 (m, 12H). $^{13}$C NMR (100 MHz, CDCl$_3$) δ 151.34, 147.57, 128.86, 127.05, 126.73, 123.71, 123.42, 110.80, 109.80, 69.80, 32.05, 29.73, 29.65, 29.55, 26.52, 22.92, 14.36.

Tetrakis(2,5-dioctyloxy-4-styryl)stilbenyl)methane.

A 25 mL round bottom flask was charged with a Teflon coated stir bar, tetrakis(4-iodophenyl)methane (96 mg, 0.116 mmol), 2,5-dioctyloxy-4-styrylstyrene (430 mg, 0.93 mmol), Pd(OAc)$_2$ (5.2 mg, 0.023 mmol), K$_2$CO$_3$ (160 mg, 1.16 mmol), n-Bu$_4$NBr (154 mg, 0.464 mmol) and anhydrous DMF (6.5 mL), The mixture was degassed with 4 freeze-pump-thaw cycles and heated at 90° C. for 24 hours. The reaction was cooled to room temperature, diluted with CH$_2$Cl$_2$, washed with brine, dried over MgSO$_4$ and the solvent was removed under reduced pressure. The crude was purified on a silica gel column (30% CH$_2$Cl$_2$/hexanes) to give a yellow greasy solid. $^1$H NMR (400 MHz, CDCl$_3$): δ 7.54 (d, J=7.66 Hz, 2H), 7.44-7.52 (complex, 4H), 7.31 (dd, J$_1$=7.32 Hz, J$_2$=7.69 Hz, 2H), 7.24–7.30 (complex, 3H), 7.10–7.16 (complex, 4H), 4.06 (t, J=6.60 Hz, 4H), 1.88 (m, 4H), 1.54 (m, 4H), 1.20–1.43 (m, 16H), 0.88 (m, 6H).

Tetrakis(4-(3',5'-di-tert-butylstyryl)stilbenyl)methane.

A 100 mL round bottom flask was charged with a Teflon coated stir bar, tetrakis(4-iodophenyl)methane (315 mg, 0.382 mmol), 4-(3', 5'-di-tert-butylstyryl)styrene (1.46 g, 4.58 mmol), Pd(OAc)$_2$ (17 mg, 20 mol %), K$_2$CO$_3$ (526 mg, 3.82 mmol), n-Bu$_4$Br (508 mg, 1.528 mmol) and anhydrous DMF (50 mL), The mixture was degassed with 4 freeze-pump-thaw cycles and heated at 90° C. for 72 hours. The reaction was cooled to room temperature, diluted with CH$_2$Cl$_2$, washed with brine, dried over MgSO$_4$ and solvent removed under reduced pressure. The crude was purified on a silica gel column (15–50% CHCl$_3$/hexanes) to give a yellow solid which contains cis-trans isomers. The isomers were dissolved in 80 mL benzene and degassed with 4 freeze-pump-thaw cycles. The solution was irradiated with long UV light for 60 minutes and solvent was removed under reduced pressure. Yield: 481 mg (80%). $^1$H NMR (400 MHz, CDCl$_3$): δ 7.06–7.55 (aromatic and vinylic —CH═, complex, 15H), 1.38 (s, 18H). $^{13}$C NMR (100 MHz, CDCl$_3$): δ 151.27, 150.64, 146.25, 137.25, 136.70, 135.36, 131.53, 129.93, 129.47, 128.62, 128.11, 127.76, 127.04, 126.98, 126.44, 126.03. 123.60, 122.39, 121.08, 35.09, 31.69.

1,1-Diphenyl-2-(4-bromophenyl)-ethene.

The following procedure was adapted from that described by Baker and Sims.[48] Working in an inert atmosphere glove box, a round bottom flask (250 mL) equipped with a teflon coated stir bar, was charged with 4-bromobenzyl (diethylphosphonate) (10.0 g, 32.56 mmol), benzophenone (5.93 g, 32.54 mmol), NaH (0.927 g, 38.6 mmol), 15-crown-5 (0.2 mL, 1 mmol), and THF (50 mL). The flask was capped with a rubber septum and vented with a needle. The reaction mixture was allowed to stir at room temperature for 24 hr, upon which time a gelatinous goo had formed in the bottom of the flask. Outside of the glove box, water was added to give a homogeneous solution that was extracted with diethylether. The combined ether extracts were washed with NaHSO$_3$ (2×100 mL), brine (2×100 mL), and dried (MgSO$_4$). A slight impurity of benzophenone was removed by flash chromatography (silica gel, hexanes, R$_f$=0.49). The hexanes solution was concentrated under vacuum to give a clear oil, that upon standing at −30° C., crystallized to yield 8.5 g (78%) of colorless crystals. $^1$H NMR (CD$_2$Cl$_2$): 7.37–7.29 (complex m, 8H); 7.55, 6.90 (AA'BB' pattern, J=8.8 Hz, 2 H each); 7.18 (m, 2H); 6.93 (s, 1H). MS: m/z 336, 334 (M$^+$, 1:1 rel. intensity).

1,1-Diphenyl-2-(4-dihydroxyboronphenyl)-ethene (DDE).

Working in an inert atmosphere glove box, a round bottom flask (250 mL) equipped with a teflon coated stir bar, was charged with 1,1-diphenyl-2-(4-bromophenyl)ethene (8.45 g, 25.2 mmol) and then fitted with a vacuum line adapter. Diethyl ether (50 mL) was then vacuum transferred into the flask and allowed to warm to 0° C. To the clear solution, n-BuLi (1.6M in THF, 18 mL, 28.8 mmol) was added dropwise over 10 min. The mixture was then allowed to warm to room temperature and stirred an additional 30 min. The mixture was then cooled again to 0° C. and $B(O/Pr)_3$ (7.3 mL, 31.6 mmol) was added dropwise and then allowed to warm to room temperature and stirred for 90 min. A solution of $H_2SO_4$ (7 mL of conc. $H_2SO_4$ in 100 mL of water) was added carefully and stirred briefly. The mixture was diluted with more diethyl ether and the organic layer separated. The aqueous phase was extracted with more diethyl ether (100 mL) and the organic fractions were combined. The diethyl ether was removed under vacuum to give a waxy oily solid that was dissolved in warm aqueous base (KOH) and filtered and allowed to cool. Neutralization with aqueous HCl then gives a flocculent white solid, which was filtered off and then dried under vacuum. Yield 2.3 g (30%). The isolated white solid is poorly soluble in chlorinated solvents, but did dissolve in methanol. $^1$H NMR ($CD_3OD$): 7.47 (d, J=7.6 Hz, 2H); 7.35–7.25 (complex m, 8H); 7.13 (br, 2H); 7.0–6.95 (overlapping m, 3H).

Tetrakis(4,4'-(2,2-diphenyl-vinyl)-1,1'-biphenyl)-methane $(C(DPVBi)_4)$.

Working in an inert atmosphere glove box, a round bottom flask (25 mL) equipped with a teflon coated stir bar, was charged with tetrakis(4-bromophenyl)methane[49] (0.500 g, 0.786 mmol), 1,1-Diphenyl-2-(4-dihydroxyboronphenyl)-ethene (1.184 g, 3.94 mmol), $Pd(dppf)Cl_2$ (24 mg, 0.033 mmol), and THF (13 mL). The flask was then sealed with a rubber septum that was then secured with copper wire. A saturated aqueous solution of $N_2$ sparged $NaHCO_3$ (10 mL) was then added via syringe into the sealed flask. The reaction mixture was then heated with stirring to 70° C. for three days. Upon cooling to room temperature, the mixture was diluted with chloroform and brine. The organic layer was separated and washed with brine (3×), then dried ($MgSO_4$). The crude product was then purified by flash chromatography (silica gel, hexanes/$CHCl_3$). Colorless needles were obtained upon diffusion of methanol into a concentrated chloroform solution. Yield 0.893 g (85%). $^1$H NMR ($CDCl_3$): δ 7.44 (AA' portion of an AA'BB' pattern, J=9.2 Hz, 2H); 7.37, 7.05 (AA'BB' pattern, J=8.4 Hz, 2 H each); 7.34–7.21 (complex overlapping m, 12H); 6.98 (s, 1H). $^{13}$C NMR ($CDCl_3$): δ 146.0, 143.7, 143.0, 140.7, 138.9, 138.3, 136.8, 131.7, 130.7, 130.3, 129.0, 128.6, 128.1, 127.93, 127.86, 127.8, 126.7, 126.2, 64.4. FABMS: m/z 1338 (M$^+$), 1083, 1006, 751, 673. Calcd for $C_{105}H_{76}$•1/3$CHCl_3$: C, 91.84; H, 5.59; Cl, 2.57. Found: C, 91.55; H, 5.49; Cl, 2.66. Same batch of TPET was further dried under vacuum and reanalyzed: Calcd for $C_{105}H_{76}$•1/4$CHCl_3$: C, 92.14; H, 5.62; Cl, 1.94. Found: C, 92.34; H, 5.47; Cl, 1.89.

2-(4-Bromophenyl)-3,3-diphenylacrylonitrile.

The synthetic procedure used to prepare this compound was adapted from a general scheme reported to yield triarylcyanoethenes.[50] A three neck flask (500 mL) equipped with a teflon coated stir bar was charged with benzophenone (16.2 g, 91.7 mmol), NaH (2.5 g, 104 mmol), and benzene (100 mL) while working in an inert atmosphere glove box. A separate liquid addition funnel was charged with 4-bromobenzylnitrile (18.7 g, 95.4 mmol) and benzene (150 mL). The funnel and the round bottom flask were temporarily sealed with rubber septa, then assembled outside of the box against a counter flow of dry $N_2$. While maintaining the inert atmosphere, a reflux condenser was then added to the assembly. The benzophenone/NaH mixture was heated to reflux for 10 min, then the 4-bromobenzylnitrile was added dropwise over 60 min while maintaining reflux. Evolving gas ($H_2$) was observed at the oil bubbler and the reaction was allowed to proceed for 20 hr. Upon cooling to room temperature, the reaction mixture was diluted with water and the organic phase was separated and washed with brine (4×100 mL). The organic phase was then dried ($MgSO_4$) and concentrated under vacuum. Addition of methanol gives a pale yellow powder that was filtered off and washed with additional methanol, then dried under vacuum. Yield 25.6 g (80%). $^1$H NMR ($C_6D_6$): δ 7.32 (m, 2H); 7.06 (m, 3H); 6.94 (AA' part of an AA'BB' pattern, 2H); 6.84 (BB' part of an AA'BB' pattern overlapping with a multiplet, 3H); 6.76 (complex t, J=8Hz, 2H); 6.70 (complex d, J=7 Hz, 2H). $^{13}$C NMR ($C_6D_6$): δ 157.7, 140.5, 139.2, 134.4, 131.9, 131.6, 130.9, 130.2, 130.1, 129.1, 128.6, 128.4, 122.7, 119.6, 111.3. MS: m/z 359, 361 (M$^+$, 1:1 rel. int.).

2-(4-Pinacolatoboronphenyl)-3,3-diphenylacrylonitrile.

Working in an inert atmosphere glove box, a round bottom flask (25 mL) equipped with a teflon coated stir bar, was charged with 1-Cyano-1-(4-bromophenyl)-2,2-diphenylethene (719 mg, 2.0 mmol), bis(pinacolato) diborane (555 mg, 2.19 mmol), $K_2OAc$ (590 mg, 6.0 mmol), $Pd(dppf)Cl_2$ (38 mg, 0.052 mmol), and dimethylacetamide (11 mL). The flask was then sealed with a rubber septum that was secured with copper wire. The reaction mixture was heated with stirring to 80° C. for 2 hr. Upon cooling to room temperature the mixture was diluted with benzene and washed with water and brine, then dried ($MgSO_4$). The resulting bright yellow filtrate was concentrated under vacuum, then diluted with methanol to afford an off white powder that was filtered off and dried under vacuum. Yield 670 mg (82%). $^1$H NMR ($CD_2Cl_2$): δ 7.61 (AA' part of an AA'BB' pattern, J=8.4 Hz, 2H); 7.47–7.43 (complex m, 5H); 7.29–7.24 (BB' part of an AA'BB' pattern overlapping with another multiplet, 3H); 7.20 (complex t, J=7.4 Hz, 2H); 7.01 (complex d, 2H); 1.31 (s, 12 H). $^{13}$C NMR ($CD_2Cl_2$): δ 158.6, 140.9, 139.4, 137.9, 135.0, 131.0, 130.2, 129.4, 129.3, 128.8, 128.6, 120.2, 112.1, 84.3, 25.0.

Tetrakis(4,4'-(3,3-diphenylacrylonitrile)-1,1'-biphenyl) methane $(C(DPAB)_4)$.

Working in an inert atmosphere glove box, a round bottom flask (50 mL), equipped with a teflon coated stir bar, was charged with tetrakis(4-bromophenyl)methane (220 mg, 0.346 mmol), 1-cyano-1-(4-boronpinacolato-phenyl)-2,2-diphenylethene (667 mg, 1.64 mmol), $Pd(dppf)Cl_2$ (10 mg, 0.014 mmol), and THF (16 mL). The flask was then sealed with a rubber septum, which was then secured with copper wire. A saturated aqueous solution of $N_2$ sparged $NaHCO_3$ (7 mL) was then added via syringe into the sealed flask. The reaction mixture was then heated with stirring to 70° C. for two days. Upon cooling to rt, the mixture was diluted with chloroform and brine. The organic layer was separated and washed with brine (3×), then dried ($MgSO_4$). The crude product was then purified by flash chromatography (silica gel, hexanes/$CHCl_3$). The combined fractions were then concentrated and layered with methanol to afford a pale off-white powder upon standing, which was filtered off and dried under vacuum. Yield 410 mg (82%). $^1$H NMR ($CD_2Cl_2$): δ 7.55–7.48 (complex overlapping m, 4H); 7.47 (s, 4H); 7.41–7.33 (complex overlapping m, 4H); 7.31–7.20 (complex overlapping m, 4H); 7.06 (complex d, J=8 Hz, 2H). $^{13}$C NMR ($CD_2Cl_2$): δ 158.0, 146.7, 141.0, 139.5, 137.8, 134.3, 131.8, 131.1, 130.5, 130.2, 129.4, 128.8, 128.7, 127.1, 126.5, 126.4, 120.3, 111.8, 64.8. FABMS: m/z 1437 (M$^+$),1158, 1080, 801. Calcd for $C_{109}H_{72}N_4$: C, 91.06; H, 5.05; N, 3.90. Found: C, 90.76; H, 4.95; N, 3.62.

Tetrastilbenyladamantane (Ad(STB)$_4$).

Working in an inert atmosphere glove box a round bottom flask (25 mL) equipped with a magnetic stir bar was charged with tetrakis(4-iodo-phenyl)adamantane[40] (250 mg, 0.265 mmol, 1.0 eq), styrene (243 μL, 2.12 mmol, 8 eq), Pd(OAc)$_4$ (5 mg, 0.008 mmol, 0.04 eq), K$_2$CO$_3$ (150 mg, 1.09 mmol, 4 eq), n-Bu$_4$NBr (340 mg, 1.05 mmol, 4 eq) and DMA (5 mL), then sealed with a rubber septum that was secured with copper wire. The reaction mixture was heated at 105° C. for 4 days. The crude product mixture was then diluted with methanol to give an off-white solid that was collected by filtration. The precipitate was suspended in hot benzene for 30 minutes, filtered, and then cooled prior to dilution with methanol. The precipitate was collected via centrifuge to afford 0.054 g (24%) of the desired product. $^1$H NMR (CD$_2$Cl$_2$): δ 7.54 (m, 24H), 7.36 (t, J=7.4 Hz, 8H), 7.26 (tt, $J_1$=7.4 Hz, $J_2$=1.2 Hz, 4H), 7.14 (br s, 8H), 2.21 (br s, 12H). $^{13}$C NMR (CD$_2$Cl$_2$): δ 149.7, 137.9, 135.7, 129.2, 128.7, 128.6, 128.1, 127.0, 126.9, 126.0, 47.6, 39.8. Exact mass (FAB, NBA) for M+H$^+$. Calcd for $C_{66}H_{56}$: 848.4382; Found: 898.4361.

Tetrastilbenylsilane (Si(STB)$_4$).

A round bottom flask (50 mL) equipped with a teflon coated stir bar was charged with tetrakis(4-bromophenyl)silane (326 mg, 0.5 mmol), styrene (2.0 g, 12 mmol), Pd(OAc)$_2$ (14 mg, 12 mol %), K$_2$CO$_3$ (690 mg, 5 mmol), n-Bu$_4$NBr (645 mg, 2 mmol), and DMA (10 mL). The flask was fitted with a rubber septum and purged with nitrogen prior to heating (80° C.) with stirring for 48 hours. The reaction mixture was allowed to cool to room temperature, diluted with CH$_2$Cl$_2$, and washed five times with brine. The organic phase was dried with MgSO$_4$, filtered through silica gel and the solvent was evaporated under reduced pressure. The residue was dissolved in CHCl$_3$ and precipitated with hexanes. The colorless needle-like crystals were collected (52% yield). $^1$H NMR (CDCl$_3$): δ 7.61 (d, J=8.0 Hz, 8H), 7.55 (m, 16H), 7.38 (t, J=7.3 Hz, J=8.0 Hz, 8H), 7.29 (t, J=7.3 Hz, 4H), 7.17 (AA'BB' pattern, J=16.4 Hz, 8H). $^{13}$C NMR (CDCl$_3$) δ 138.5, 137.1, 136.7, 133.4, 129.5, 128.6, 128.4, 127.7,126.5, 125.9.

Tetrakis(4-tert-butylstyrylstilbenyl)adamantane (Ad($^t$BuSSB)$_4$).

A dry round bottom flask (50 mL) was charged with of tetrakis(4-iodo-phenyl)adamantane (213 mg, 0.230 mmol, 1.0 eq) and 4,4'-tert-butyl-vinylstilbene (375 mg, 1.40 mmol, 6.0 eq) prior to sealing with a rubber septum and purging with argon. To the flask was added dry DMA (6 mL) via syringe. In an inert atmosphere glove box, a 25 mL round bottom flask equipped with a magnetic stir bar was charged with Na$_2$OAc (120 mg, 1.0 mmol, 4.5 eq) and Hermann's catalyst (10 mg, 0.01 mmol, 0.05 eq) prior to sealing with a rubber septum. The solution was transferred from the first flask to the second flask via syringe and then heated to 140° C. using an oil bath for 5 days. The slurry was cooled to room temperature prior to quenching with water. The resulting precipitate was collected via filtration. The filtrate was diluted with more water and the filtrate collected. The precipitate was dried under vacuum to afford 104 mg (31%) of the desired product. $^1$H NMR (CDCl$_3$): δ 7.52 (m, 32H), 7.48 (d, J=8.5 Hz, 8H), 7.40 (d, J=8.5 Hz, 8H), 7.14 (d, J=16.3 Hz, 4H), 7.13 (m, 8H), 7.08 (d, J=16.3 Hz, 4H), 2.22 (m,12H), 1.35 (s, 36H). $^{13}$C NMR (CDCl$_3$): δ 151.0, 149.1, 137.0, 136.8, 135.6, 134.8, 128.8, 128.5, 128.2, 127.7, 127.0, 126.9, 126.8, 126.4, 125.8, 125.7. 47.4, 39.5, 34.8, 31.5. Calcd for $C_{114}H_{112}$: C, 92.38; H, 7.62. Found: C, 92.26; H, 7.64. FABMS: (M+H)$^+$1482.

Tetrakis(4-tert-butylstyrylstilbenyl)silane (Si($^t$BuSSB)$_4$).

A round bottom flask (50 mL) equipped with a teflon coated stir bar was charged with tetrakis(4-bromophenyl)silane (0.652 g, 1.00 mmol), 4,4'-tert-butylvinylstilbene (1.57 g, 5.98 mmol), Pd(OAc)$_2$ (27 mg, 12 mol %), K$_2$CO$_3$ (1.38 g, 10 mmol), n-Bu$_4$NBr (1.29 g, 4 mmol), and DMA (30 mL). The flask was fitted with a rubber septum and purged with nitrogen prior to heating (80° C.) with stirring for 72 hours. The reaction mixture was allowed to cool to room temperature, diluted with CH$_2$Cl$_2$, and washed five times with brine. The organic phase was dried with MgSO$_4$, filtered and solvent evaporated under reduced pressure. The crude residue was dissolved in CHCl$_3$ and precipitated with methanol. The solid material was filtered off then further purified by silica gel chromatography (chloroform:hexanes= 1:3) to give Si($^t$BuSSB)$_4$ as a greenish white solid (40% yield). $^1$H NMR (CDCl$_3$): δ 7.59 (d, J=8 Hz, 4H), 7.52 (s, 4H), 7.43 (d, J=8 Hz, 4H), 7.17 (d, J=17 Hz, 2H), 7.10 (dd, J=16 Hz, 2H), 1.34 (s, 9H). FABMS: m/z=1378 (M+H$^+$).

Fabrication of Films.

The two hexyloxy groups in the T—4R—OC$_6$H$_{13}$ "arms" make the compound freely soluble in common organic solvents such chloroform, chlorobenzene, toluene, and p-xylene. Similar results can be obtained with T—4R—OC$_8$H$_{17}$, however more transparent films were obtained out of chloroform, instead of aromatic solvents. The solutions were stirred with a magnetic bar at room temperature for several hours until a clean, colorless solution was formed.

Toluene, chloroform, chlorobenzene and p-xylene solutions of T—4R—OC$_6$H$_{13}$ can be spin cast onto glass or indium/tin-oxide (ITO) coated glass to give clear transparent films. Pinhole-free, uniform films were obtained by spin-casting the solutions at room temperature. High quality films with thickness of 300–5000 Å were obtained by varying the spin speed and the solution concentration. The spin speed was typically in the range of 400 rpm to 5000 rpm. For example, spin-casting from a 60 mg/mL solution in toluene at spin speeds of 1000 rpm and 3000 rpm yields films with thickness of 2800 Å and 1600 Å, respectively. Spin casting at 1000 rpm from a 7.5 mg/mL solution in toluene gave 350 Å films.

Optical Properties of T—4R—OC$_6$H$_{13}$ and T—4R—OC$_8$H$_{17}$

Spectral measurements were carried out with these films. FIG. 7 shows the absorption and photoluminescence (PL) spectra from a film of tetrakis(4-(4'-(3", 5"-dihexyloxystyryl)styryl)stilbenyl)methane, (T—4R—OC$_6$H$_{13}$), and FIG. 6 shows the corresponding spectra for tetrakis((4-(2'5'-dioctyloxy-4'styryl)styryl)stilbenylmethane (T—4R—OC$_8$H$_{17}$). For photoluminescence measurements, an excitation source of wavelength corresponding to the absorption maximum was incident upon the sample at 90° to the detector.

Performance of EL Devices

Devices with the configuration of ITO/(AB)/MTF/Ba/Al were fabricated where AB. refers to the anode buffer layer (polyaniline (PANI), polyethylenedioxythiophene (PEDT), or polyvinylcarbazole (PVK)), and MTF represents the molecular thin film comprising either tetrakis(4-(4'-(3", 5"-dihexyloxystyryl)styryl)stilbenyl)methane or tetrakis(4-(4'-(3", 5"-dihexyloxystyryl)styryl)stilbenyl)methane. The performance of a variety of device architectures were tested and a summary of results is presented in Table 3.

TABLE 3

| Entry | Material | Casting Solvent | Anode Buffer | V (V/$\mu$m) | cd/$m^2$ | QE(%) |
|---|---|---|---|---|---|---|
| 1 | T-4R—$OC_6H_{13}$ | p-xylene | NONE | 8.5 (85) | 49 | 0.06 |
| 2 | | p-xylene | PANI | 6.8 (68) | 175 | 0.22 |
| 3 | | p-xylene | PEDT | 4.6 (25) | 379 | 0.48 |
| 4 | | p-xylene | PVK | 8.7 (57) | 285 | 0.26 |
| 5 | | p-xylene | PEDT/PVK | 8.3 (35) | 558 | 0.71 |
| 6 | | chlorobenzene | PEDT | 3.6 (20) | 177 | 0.23 |
| 7 | | chlorobenzene | PVK | 10. (66) | 110 | 0.14 |
| 8 | | chlorobenzene | PEDT/PVK | 5.4 (22) | 518 | 0.66 |
| 9 | T-4R—$OC_8H_{17}$ | chloroform | NONE | 7.3 (78) | 45 | 0.06 |
| 10 | | chloroform | PEDT | 4.7 (27) | 135 | 0.17 |
| 11 | | chloroform | PEDT/PVK | 6.0 (26) | 263 | 0.33 |
| 12 | | p-xylene | PEDT | 5.0* | 770 | 0.16 |

*Current density = 483 mA/$cm^2$

Figure 10:
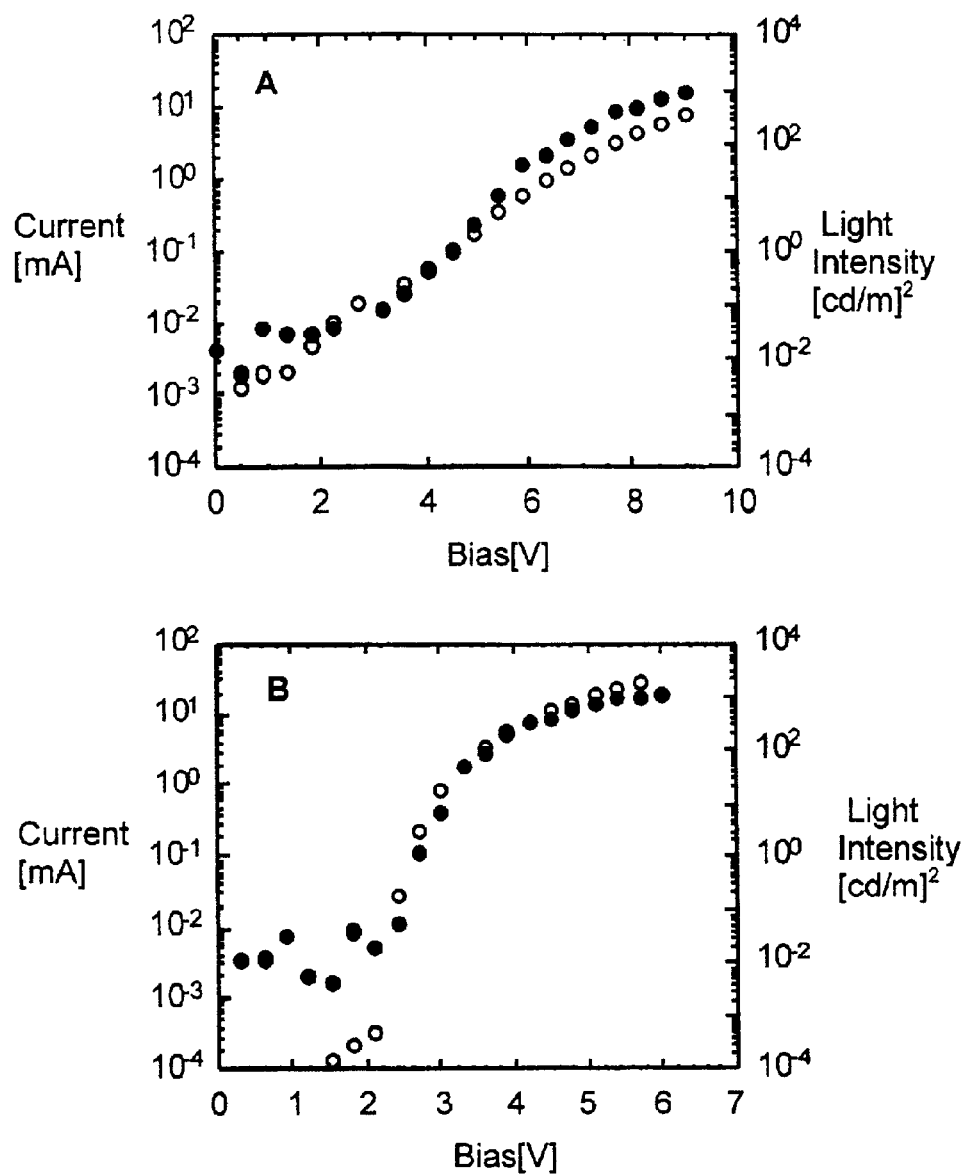
FIG. 10 shows voltage versus current (○—left axes) and light intensity (●—right axes) for (A) tetrakis(4-(4'-(3",5"-dihexyloxystyryl)styryl)stilbenyl)methane (1000 Å) using PEDT/PVK as the anode buffer; (B) tetrakis((4-(2'5'-dioctyloxy-4'styryl)styryl)stilbenylmethane (940 Å) using PEDT/PVK as the anode buffer. Current is measured in mA and light intensity in cd/m$^2$.

As shown in FIG. 10, devices fabricated from tetrakis(4-(4'-(3", 5"-dihexyloxystyryl)styryl)stilbenyl)methane and tetrakis((4-(2'5'-dioctyloxy-4'styryl)styryl)stilbenylmethane begin emitting at ca. 3 V, near the HOMO-LUMO energy difference of the materials. Current turns on exactly as the electroluminescence (EL) turns on, indicating no current leakage by electrode contacts or pinholes.

Figure 11:
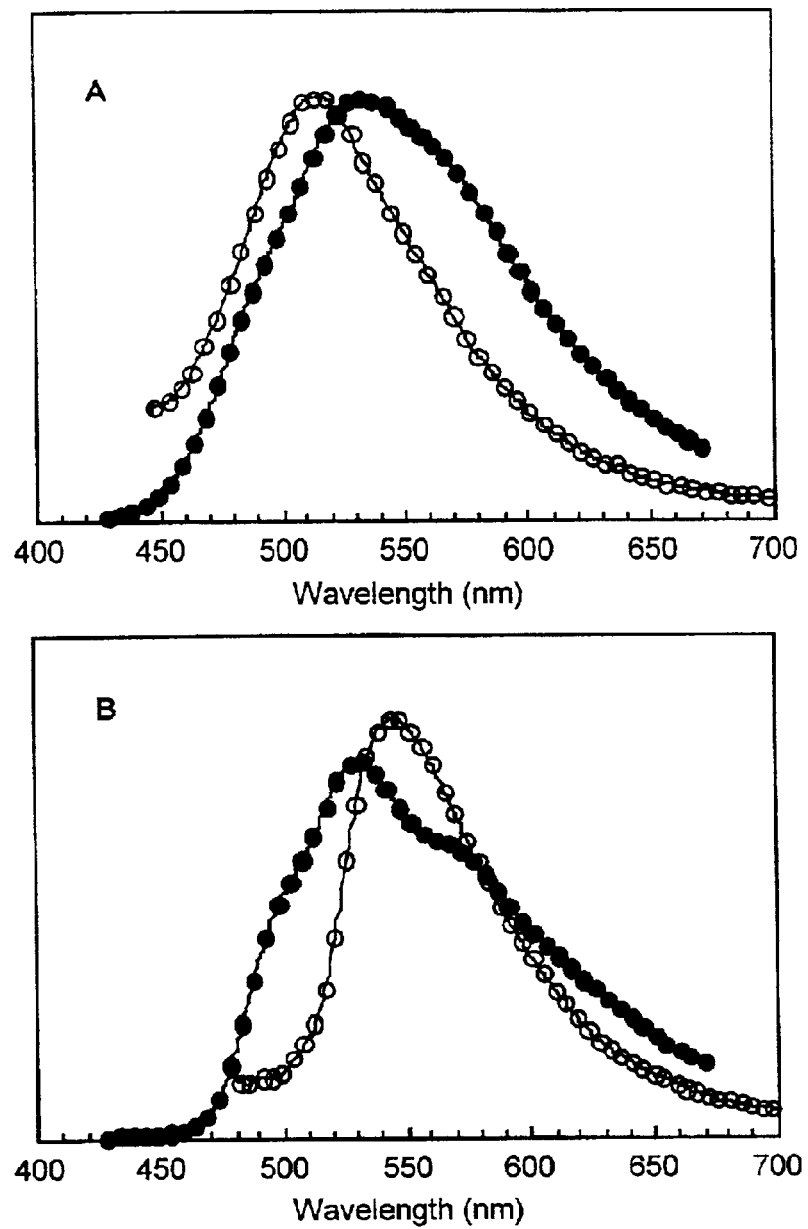
FIG. 11 shows: (A) photoluminescence (○) and electroluminescence (●) spectra of tetrakis(4-(4'-(3",5"-dihexyloxystyryl)styryl)stilbenyl)methane, and (B) corresponding spectra for tetrakis((4-(2'5'-dioctyloxy-4'styryl)styryl)stilbenylmethane.

FIG. 11 shows typical EL spectra; which are similar to the PL from annealed films. Note also that because the emission overlaps quite well with the response of the human eye these devices offer promise for white light emission.

Optimization of Device Architecture

The simplest device architecture corresponds to ITO/MTF/Ba/Al. Light is detectable at c.a. 3 V, a low voltage for a non-polymeric spin cast molecular thin film. However, as shown by entries 1 and 9 in Table 3, for either tetrakis(4-(4'-(3", 5"-dihexyloxystyryl)styryl)stilbenyl)methane or tetrakis((4-(2'5'-dioctyloxy-4'styryl)styryl) stilbenylmethane, the single layer devices exhibit low quantum efficiencies. Comparison of entry 1 against entry 3 shows that the introduction of a PEDT layer enhances device performance. PVK and PANI may also be used, but with less success (entries 2 and 4, Table 3). The best tetrakis(4-(4'-(3", 5"-dihexyloxystyryl)styryl)stilbenyl)methane device (entry 5 in Table 3), takes advantage of two anode buffer layers (PEDT/PVK), exhibits a brightness of 558 cd/$m^2$ at 5.4 V (22 V/$\mu$m) and an external quantum efficiency of 0.71% photons per electron. Higher efficiencies are anticipated after balancing charge injection by using electrode materials that better match HOMO and LUMO energies.

Devices made with tetrakis((4-(2'5'-dioctyloxy-4'styryl) styryl)stilbenylmethane were more conveniently made from chloroform than p-xylene. Often, the films from p-xylene were slightly opaque which led to devices with current leakage. As in the case of T—4R—$OC_6H_{13}$, device efficiency is enhanced by the use of PEDT and PVK anode buffers (entries 9–12 in Table 3).

Although the foregoing invention has been described in some detail by way of illustration and example for purposes of clarity and understanding, it will be obvious that various modifications and changes, which are within the knowledge of those skilled in the art, are also considered to fall within the scope of the invention.

The references in the following Bibliography are incorporated herein by reference.

Bibliography

1 See for example the excellent series of review articles in the recent Accounts of Chemical Research issue: *Molecular Materials in Electronic and Optoelectronic Devices*; Sheats, J. F.; Barbara, P. F., Eds.; *Acc. Chem. Res.* 1999, 32(3). (a) Sheats, J. R.; Chang, Y.-L.; Roitman, D. B.; Stocking, A. *Acc. Chem. Res.* 1999, 32, 193–200. (b) Fox, M. A. *Acc. Chem. Res.* 1999, 32, 201–207. (c) Garnier, F. *Acc. Chem. Res.* 1999, 32, 209–215. (d) Y. Z. Wang, Y. Z.; Epstein, A. J. *Acc. Chem. Res.* 1999, 32, 217–224. (e) Kugler, T.; Lögdlund, M.; Salaneck, W. R. *Acc. Chem. Res.* 1999, 32, 225–234. (f) Liu, C.-Y.; Bard, A. J. *Acc. Chem. Res.* 1999, 32, 235–245. (g) Gao, Y. *Acc. Chem. Res.* 1999, 32, 247–255. (h) Van Hutten, P. F.; Krasnikov, V. V.; Hadziioannou, G. *Acc. Chem. Res.* 1999, 32, 257–265. (i) Brédas, J.-L.; Cornil, J.; Beljonne, D.; dos Santos, D. A.; Shuai, Z. *Acc. Chem. Res.* 1999, 32, 267–276.

2 For a popular account see: Yam, P. *Sci. Am.* 1997, 8, 90–96.

3 (a) Tang, C. W.; Van Slyke, S. A. *Appl. Phys. Lett.* 1987, 51, 913–915. (b) Tang, C. W.; Van Slyke, S. A.; Chen, C. H. *J. Appl. Phys.* 1989, 65, 3610–3616.

4 Burroughs, J. H.; Bradley, D. D. C.; Brown, A. R.; Marks, R. N.; Mackay, K.; Friend, R. H.; Burns, P. L.; Holmes, A. B. *Nature* 1990, 347, 539–541.

5 (a) Service, R. F. *Science* 1996, 273, 878–880. (b) Sheats, J. R.; Antoniadis, H.; Mueschen, M.; Leonard, W.; Miller, J.; Moon, R.; Roitman, D.; Stocking, A. *Science* 1996, 273, 884–888.

6 (a) Tang, C. W. *Appl. Phys. Lett.* 1986, 48, 183–185. (b) Wöhrle, D.; Meissner, D. *Adv. Mater.* 1991, 3, 129–138.

7 (a) Lovinger, A. J.; Rothberg, L. J. J. *Mater. Res.* 1996, 11, 1581–1592. (b) Katz, H. E. *J. Mater. Chem.* 1997, 7, 369–376. (c) Garnier, F.; Hajlaoui, R.; Yassar, A.; Srivastava, P. *Science* 1994, 265, 1684–1686. (d) Laquindanum, J. G.; Katz, H. E.; Dodabalapur, A.; Lovinger, A. J. *J. Am. Chem. Soc.* 1996, 118, 11331–11332. (e) Torsi, L.; Dodabalapur, A.; Rothberg, L. J.; Fung, A. W. P.; Katz, H. E. *Science* 1996, 272, 1462–1464. (f Bao, Z.; Lovinger, A. J.; Brown, J. *J. Am. Chem. Soc.* 1998, 120, 207–208. (g) Li, X.-C.; Sirringhaus, H.; Garnier, F.; Holmes, A. B.; Moratti, S. C.; Feeder, N.; Clegg, W.; Teat, S. J.; Friend, R. H. *J. Am. Chem. Soc.* 1998, 120, 2206–2207.

8 For comprehensive reviews of organic device physics: (a) Greenham, N. C.; Friend, R. H. *Solid State Physics* 1995, 49, 1–149. (b) Forrest, S. R. *Chem. Rev.* 1997, 97, 1793–1896.

9 See for example, and references contained therein: Tessler, N. *Adv. Mater.* 1999, 11, 363–370.

10 Selected key references and reviews which relate chemical structure with electronic properties: (a) Schenk, R.; Gregorius, H.; Meerholz, K.; Heinze, J.; Müllen, K. *J. Am.*

*Chem. Soc.* 1991, 113, 2634–2647. (b) Meier, H. *Angew. Chem. Int Ed. Engl.* 1992, 31, 1399–1420. (c) Burn, P. L.; Holmes, A. B.; Kraft, A.; Bradley, D. D. C.; Brown, A. R.; Friend, R. H.; Gymer, R. W. *Nature* 1992, 356, 47–49. (d) Burn, P. L.; Kraft, A.; Baigent, D. R.; Bradley, D. D. C.; Brown, A. R.; Friend, R. H.; Gymer, R. W.; Holmes, A. B.; Jackson, R. W. *J. Am. Chem. Soc.* 1993, 115, 10117–10124. (e) Son, S.; Dodabalapur, A.; Lovinger, A. J.; Galvin, M. E. *Science* 1995, 269, 376–378. (f Schmidt, A.; Anderson, M. L.; Dunphy, D.; Wehrmeister, T.; M üllen, K.; Armstrong, N. R. *Adv. Mater.* 1995, 7, 722–726. (g) Scherf, U.; Müllen, K. *Synthesis* 1992, 23–38. (h) Tour, J. M. *Chem. Rev.* 1996, 96, 537–553. (i) Feast, W. J.; Tsibouklis, J.; Pouwer, K. L.; Groenendaal, L.; Meijer, E. W. *Polymer* 1996, 37, 5017–5047. (j) Roncali, J. *Chem. Rev.* 1997, 97, 173–205. (k) Kraft, A.; Grimsdale, A. C.; Holmes, A. B. *Angew. Chem. Int Ed. Engl.* 1998, 37, 402–428. (l) Katz, H. E.; Bent, S. F.; Wilson, W. L.; Schilling, M. L.; Ungashe, S. B. *J. Am. Chem. Soc.* 1994, 116, 6631–6635. (m) Strukelj, M.; Papadimitrakopoulos, F.; Miller, T. M.; Rothberg, L. J. *Science* 1995, 267, 1969–1971. (n) Strukelj, M.; Miller, T. M.; Papadimitrakopoulos, F.; Son, S. *J. Am. Chem. Soc.* 1995, 117, 11976–11983. (o) Stalmach, U.; Kolshorn, H.; Brehm, I.; Meier, H. *Liebigs Ann.* 1996, 1449–1456. (p) Maddux, T.; Li, W.; Yu, L. *J. Am. Chem. Soc.* 1997, 119, 844–845. (q) Martin, R. E.; Diederich, F. *Angew. Chem. Int. Ed. Engl.* 1999, 38, 1350–1377.

11 Jenekhe, S. A.; Osaheni, J. A. *Science* 1994, 265, 765.

12 J. H. Burroughs, D. D. C. Bradley, A. R. Brown, R. N. Marks, K. Mackay, R. H. Friend, P. L. Burns and A. B. Holmes, *Nature* 347, 539 (1990)

13 U.S. Pat. No. 5,189,136

14 H. Spreitzer, W. Kreuder, H. Becher, H. Schoo, R. Demandt, German Pat. WO 98/27136

15 European Patent 0544795, WO 9804610A1, H. Becker, H. Spreitzer, Y. Cao, *Adv. Mater.* 12(1), 42 (2000)

16 D. Braun, G. Gustafssom, D. Mcbranch, *J. Appl. Phys.* 72, 564 (1992)

17 (a) Chi Zhang, Gang Yu and Yong Cao, U.S. Pat. No. 5,798,170, (b) Ian Park, Yong Cao and C. Y. Yang, *J. Appl. Phys.* 85(4), 2441 (1999)

18 S. A. VanSlyke,; C. H. Chen; C. W. Tang, *Appl. Phys. Left.* 1996, 69 2160

19 Han, E.-m.; Do, L.-m.; Niidome, Y.; Fujihura, M. *Chem. Lett.* 1994, 969–972.

20 A particularly elegant demonstration of these effects can be found in: Joswick, M. D.; Cambell, I. H.; Barashkov, N. N.; Ferraris, J. P. *J. Appl. Phys.* 1996, 80, 2883–2890.

21 Tokito, S.; Tanaka, H.; Noda, K.; Okada, A.; Taga, T. *Appl. Phys. Lett.* 1997, 70, 1929–1931.

22 Fenter, P.; Schreiber, F.; Bulovic, V.; Forrest, S. R. *Chem. Phys. Lett.* 1997, 277, 521–526.

23 (a) Enkelmann, V.; Rühe, J.; Wegner, G. *Synth. Met.* 1990, 37, 79–89. (b) Garnier, F.; Horowitz, G.; Fichou, D.; Yassar, A. *Synth. Met.* 1996, 81, 163–171. (c) Schoonveld, W. A.; Stok, R. W.; Weijtmans, J. W.; Vrijmoeth, J.; Wildeman, J.; Klapwijk, T. M. *Synth. Met.* 1997, 84, 583–584.

24 (a) Yan, M.; Rothberg, L. J.; Papadimitrakopoulos, F.; Galvin, M. E.; Miller, T. M. *Phys. Rev. Lett.* 1994, 72, 1104–1107. (b) Rothberg, L. J.; Yan, M.; Papadimitrakopoulos, F.; Galvin, M. E.; Kwock, E. W.; Miller, T. M. *Synth. Met.* 1996, 80, 41–58. (c) Conwell, E. M.; Perlstein, J.; Shaik, S. *Phys. Rev. B* 1996, 54, R2308-R2310. (d) Conwell, E. *Trends Polym. Sci.* 1997, 5, 218–222. (e) Cornil, J.; dos Santos, D. A.; Crispin, X.; Silbey, R.; Brédas, J. L. *J. Am. Chem. Soc.* 1998, 120, 1289–1299. (f Jakubiak, R.; Collison, C. J.; Wan, W. C.; Rothberg, L. J.; Hsieh, B. R. *J. Phys. Chem.* 1999, 103, 2394–2398.

25 Doi, S.; Kuwabara, M.; Noguchi, T.; Ohnishi, T. *Synth. Met.* 1993, 55–57, 4174–4179.

26 (a) Shirota, Y.; Kobata, T.; Noma, N. *Chem. Lett.* 1989, 1145–1148. (b) Inada, H.; Shirota, Y. *J. Mater. Chem.* 1993, 3, 319–320. (c) Ueta, E.; Nakano, H.; Shirota, Y. *Chem. Lett.* 1994, 2397–2400. (d) Inada, H.; Ohnishi, K.; Nomura, S.; Higuchi, A.; Nakano, H.; Shirota, Y. *J. Mater. Chem.* 1994, 4, 171–177. (e) Kageyama, H.; Itano, K.; Ishikawa, W.; Shirota, Y. *J. Mater. Chem.* 1996, 6, 675–676. (f) Tanaka, H.; Tokito, S.; Taga, Y.; Okada, A. *Chem. Commun.* 1996, 2175–2176. (g) Tanaka, S.; Iso, T.; Doke, Y. *Chem. Commun.* 1997, 2063–2064. (h) Naito, K.; Miura, A. *J. Phys. Chem.* 1993, 97, 6240–6248. (i) Naito, K. *Chem. Mater.* 1994, 6, 2343–2350. (j) Naito, K.; Sakurai, M.; Egusa, S. *J. Phys. Chem. A* 1997, 101, 2350–2357. (k) Kraft, A. *Chem. Commun.* 1996, 77–79. (l) Bettenhausen, J.; Strohriegl, P. *Adv. Mater.* 1996, 8, 507–510. (m) Bettenhausen, J.; Greczmiel, M.; Jandke, M.; Strohriegl, P. *Synth. Met.* 1997, 91, 223–228. (n) Salbeck, J. Ber. Bunsenges. *Phys. Chem.* 1996, 100, 1667–1677. (o) Salbeck, J.; Yu, N.; Bauer, J.; Weissörtel, F.; Bestgen, H. *Synth. Met.* 1997, 91, 209–215. (p) Wang, P.-W.; Liu, Y.-J.; Devadoss, C.; Bharathi, P.; Moore, J. S. *Adv. Mater.* 1996, 8, 237–241. (q) Meier, H.; Lehmann, M. *Angew. Chem. Int. Ed. Engl.* 1998, 37, 643–645. (r) O'Brian, D. F.; Burrows, P. E.; Forrest, S. R.; Koene, B. E.; Loy, D. E.; Thompson, M. E. *Adv. Mater.* 1998, 10, 1108–1111. (s) Koene, B. E.; $^{Loy}$, D. E.; Thompson, M. E. *Chem. Mater.* 1998, 10, 2235–2250. (t) Hu, N.-X.; Xie, S.; Popovic, Z.; Ong, B.; Hor, A.-M. *J. Am. Chem. Soc.* 1999, 121, 5097–5098. (u) Donald Lupo, Josef Salbeck, Hermann Schenk, Thomas Stehlin, Roland Stern, Arno Wolf U.S. Pat. No. 5,480,217. (v) Y. Shirota, *J. Mater. Chem.* 10, 1 (2000).

27 Preliminary aspects of this work have been communicated: Oldham, W. J., Jr.; Lachicotte, R. J.; Bazan, G. C. *J. Am. Chem. Soc.* 1998, 120, 2987–2988.

28 R. F. Heck, *Org. React.* 1982, 27, 345–389.

29 T. Jeffery, Adv. *Metal-Organic Chem.* 1996, 5, 153.

30 T. Maddux, W. Li, L. Yu, *J. Am. Chem. Soc.* 1997, 119, 844.

31 Shaheen, S. E.; Jabbour, G. E.; Morrell, M. M.; Kawabe, Y.; Kippelen, B.; Peyghambarian, N.; Nabor, M.-F.; Schlaf, R.; Mash, E. A.; Armstrong, N. R. *J. Appl. Phys.* 1998, 84, 2324–2327.

32 *Modern Molecular Photochemistry*; Turro, N. J.; University Science Books: Sausalito, Calif., 1991, pp 170–172.

33 Lawrence, N. J. In *Preparation of Alkenes: A Practical Approach*; Williams, J. M. J., Ed.; Oxford University Press: New York, 1996; pp 37–38.

34 Based upon the procedures found in: (a) Brown, H. C.; Cole, T. E. *Organometallics* 1983, 2, 1316–1319. (b) *Synthesis of Organometallic Compounds* Komiya, S., Ed.; John Wiley and Sons: New York, 1997, p 354.

35 Miyaura, N.; Suzuki, A. *Chem. Rev.* 1995, 95, 2457–2483.

36 For a similar evaluation of Suzuki coupling protocols see: Kowitz, C.; Wegner, G. *Tetrahedron* 1997, 53, 15553–15574.

37 Beller, M.; Fischer, H.; Herrmann, W. A.; Öfele, K; Brossmer, C. Angew. *Chem. Int. Engl.* 1995, 34, 1848–1849.

38 Greenham, N. C.; Moratti, S. C.; Bradley, D. D. C.; Friend, R. H.; Holmes, A. B. *Nature*, 1993, 365, 628.
39 Ishiyama, T.; Murata, M.; Miyaura, N. *J. Org. Chem.* 1995, 60, 7508–7510.
40 Mathias, L. J.; Reichert, V. R.; Muir, A. V. G. *Chem. Mater.* 1993, 5, 4–5.
41 See, for example, J. H. Burroughs, D. D. C. Bradley, A. R. Brown, R. N. Marks, K. Mackay, R. H. Friend, P. L. Burns, and A. B. Holmes, *Nature* 347, 539 (1990); D. Braun and A. J. Heeger,*Appl. Phys. Lett.* 58, 1982 (1991); A. J. Heeger and D. Braun, U.S. Pat. No. 5,869,350
42 I. D. Parker, *J. Appl. Phys.* 75, 1656 (1994); G. Yu *Synthetic Metals*, 80, 143 (1996)
43 See, e.g., P. Smith, A. J. Heeger, Y. Cao, J. Chiang and A. Andreatta, U.S. Pat. No. 5,470,505
44 As demonstrated by G. Gustafsson, Y. Cao, G. M. Treacy, F. Klavetter, N. Colaneri, and A. J. Heeger, *Nature*, 357, 477 (1992), by Y. Yang and A. J. Heeger,*Appl. Phys. Left.* 64, 1245 (1994) and U.S. Pat. No. 5,723,873, by Y. Yang, E. Westerweele, C. Zhang, P. Smith and A. J. Heeger, *J. Appl. Phys.* 77, 694 (1995), by J. Gao, A. J. Heeger, J. Y Lee and C. Y Kim, *Synth. Met.*, 82, 221 (1996) and by Y. Cao, G. Yu, C Zhang, R. Menon and A. J. Heeger, *Appl. Phys. Left.* 70, 3191, (1997).]
45 I. D. Parker, *J. Appl. Phys.* 75, 1656 (1994)
46 M. D. McGehee, T. Bergstedt, C. Zhang, A. P. Saab, M. O'Regan G. Bazan, V. Srdanov and A. J. Heeger, *Adv. Mater.* 11, 1349 (1999)
47 Burger, B. J.; Bercaw, J. E. In *Experimental Organometallic Chemistry*; Wayda, A. L.; Darrensbourg, M. Y. Eds.; ACS Sym. Ser. 357; Am. Chem. Soc.: Washington, D.C., 1987.
48 Baker, R.; Sims, R. J. *Synthesis* 1981, 117.
49 Wilson, L. M.; Griffin, A. C. J. *Mater. Chem.* 1993, 3, 991–994.
50 Gilbert, J.; Miquel, J.-F.; Précigoux, G.; Hospital, M.; Raynaud, J.-P.; Michel, F.; de Paulet, A. C. *J. Med. Chem.* 1983, 26, 693–699.

What is claimed is:

1. A tetrahedral compound having formula (I),

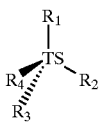

(I)

wherein TS is a tetrahedral junction unit selected from the group consisting of tetraphenylsilane, an $sp^3$ hybridized silicon atom, tetraphenyladamantane, adamantane and cubane; and R1, R2, R3 and R4 are optoelectronic arms, wherein each optoelectronic arm is a linear oligomer, polymer or copolymer.

2. The tetrahedral compound of claim 1 wherein each optoelectronic arm is a semiconducting oligomer, polymer or copolymer.

3. The tetrahedral compound of claim 1, each optoelectronic arm comprising a stilbenoid chromophore.

4. The tetrahedral compound of claim 1 wherein R1, R2, R3 and R4 are optoelectronic arms corresponding to general formula II:

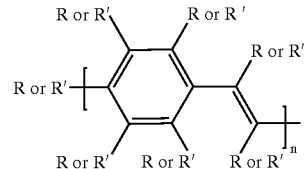

wherein R is hydrogen; R' is alkoxy, alkyl, aryl, aryloxy, cyano, halide or amino; and n is an integer from 2 to 100.

5. A tetrahedral compound having formula (I),

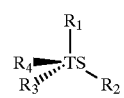

(I)

wherein TS is a tetrahedral junction unit selected from the group consisting of tetraphenylsilane, an $sp^3$ hybridized silicon atom, tetraphenyladamantane, adamantane and cubane; and R1, R2, R3 and R4 are each optoelectronic arms corresponding to general formula II:

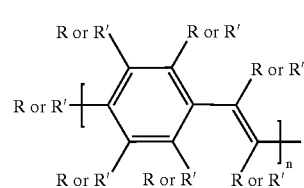

II wherein R is hydrogen; R' is alkoxy, alkyl, aryl, aryloxy, cyano, halide, or amino; and n is an integer from 2 to 100.

6. A composition comprising a tetrahedral compound according to claim 1.

7. A composition according to claim 6 further comprising an electron or hole transport agent.

8. A thin-film electronic device comprising the tetrahedral compound of claim 1.

9. A thin film electronic device comprising the composition of claim 7.

10. The device of claim 8 comprising at least two layers selected from the group consisting of an electroluminescent layer, an electron transport layer, and a hole transport layer, wherein at least one of said electroluminescent layer, said electron transport layer, or said hole transport layer comprises the tetrahedral compound.

* * * * *